US011596456B2

(12) United States Patent
Beckett et al.

(10) Patent No.: US 11,596,456 B2
(45) Date of Patent: Mar. 7, 2023

(54) ADJUSTABLE DEVICES FOR TREATING ARTHRITIS OF THE KNEE

(71) Applicant: NuVasive Specialized Orthopedics, Inc., San Diego, CA (US)

(72) Inventors: Adam G. Beckett, San Diego, CA (US); Thomas B. Buford, San Diego, CA (US); Youngsam Bae, San Diego, CA (US); Edward H. Kim, San Diego, CA (US); Matthew Tobias Jacobs, San Diego, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 259 days.

(21) Appl. No.: 16/812,114

(22) Filed: Mar. 6, 2020

(65) Prior Publication Data
US 2020/0205866 A1 Jul. 2, 2020

Related U.S. Application Data

(63) Continuation of application No. 15/953,453, filed on Apr. 15, 2018, now Pat. No. 10,617,453, which is a
(Continued)

(51) Int. Cl.
*A61B 17/72* (2006.01)
*A61B 17/86* (2006.01)
(Continued)

(52) U.S. Cl.
CPC .......... *A61B 17/72* (2013.01); *A61B 17/7216* (2013.01); *A61B 17/7233* (2013.01);
(Continued)

(58) Field of Classification Search
CPC . A61B 17/72; A61B 17/7216; A61B 17/7233; A61B 17/8605; A61B 17/8095;
(Continued)

(56) References Cited

U.S. PATENT DOCUMENTS 2,702,031 A 2/1955 Wenger
3,111,945 A 11/1963 Von Solbrig
(Continued)

FOREIGN PATENT DOCUMENTS

CN 2367264 Y 3/2000
CN 1697630 A 11/2005
(Continued)

OTHER PUBLICATIONS

Abe et al., "Experimental external fixation combined with percutaneous discectomy in the management of scoliosis.", Spine, 1999, pp. 646-653, 24, No. 7.
(Continued)

*Primary Examiner* — Ellen C Hammond
*Assistant Examiner* — David C Comstock
(74) *Attorney, Agent, or Firm* — Hoffman Warnick LLC

(57) ABSTRACT

A system, and method of using the system, for changing the angle of a bone of a subject is provided by the present disclosure. In one embodiment the system includes a non-invasively adjustable implant configured to be placed inside a longitudinal cavity within the bone and comprising an outer housing and an inner shaft telescopically disposed in the outer housing, at least one of the outer housing and inner shaft associated with a first anchor hole and a second anchor hole, the first anchor hole configured to pass a first anchor for coupling the adjustable implant to a first portion of bone and the second anchor hole configured for to pass a second anchor for coupling the adjustable implant to the first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element
(Continued)

configured to be remotely operable to telescopically displace the inner shaft in relation to the outer housing; and wherein the first anchor hole is configured to allow the first anchor to pivot in at least a first angular direction and the second anchor hole is configured to allow the second anchor to translate in at least a first translation direction.

20 Claims, 27 Drawing Sheets

Related U.S. Application Data continuation of application No. PCT/US2016/057371, filed on Oct. 17, 2016.

(60) Provisional application No. 62/242,931, filed on Oct. 16, 2015.

(51) Int. Cl.
  *A61B 17/00* (2006.01)
  *A61B 17/68* (2006.01)
  *A61B 17/80* (2006.01)

(52) U.S. Cl.
  CPC ...... *A61B 17/8605* (2013.01); *A61B 17/8095* (2013.01); *A61B 2017/00199* (2013.01); *A61B 2017/00398* (2013.01); *A61B 2017/00402* (2013.01); *A61B 2017/00411* (2013.01); *A61B 2017/00477* (2013.01); *A61B 2017/00539* (2013.01); *A61B 2017/00867* (2013.01); *A61B 2017/00876* (2013.01); *A61B 2017/00991* (2013.01); *A61B 2017/681* (2013.01)

(58) Field of Classification Search
  CPC ........... A61B 2017/00199; A61B 2017/00398; A61B 2017/00402; A61B 2017/00411; A61B 2017/00477; A61B 2017/00539; A61B 2017/00867; A61B 2017/00876; A61B 2017/00991; A61B 2017/681
  USPC ....................................... 606/63, 64
  See application file for complete search history.

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,512,901 A | 5/1970 | Law |
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,964,763 A | 10/1999 | Incavo |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |

(56) References Cited

U.S. PATENT DOCUMENTS

| | | |
|---|---|---|
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Worth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |

(56) References Cited

U.S. PATENT DOCUMENTS

| | | |
|---|---|---|
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,852,187 B2 | 10/2014 | Pool et al. |
| 8,870,881 B2 | 10/2014 | Rezach et al. |
| 8,870,959 B2 | 10/2014 | Arnin |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 9,848,914 B2 | 12/2017 | Pool |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stauch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1 | 9/2004 | Meyer |
| 2005/0034705 A1 | 2/2005 | McClendon |
| 2005/0049617 A1 | 3/2005 | Chatlynne et al. |
| 2005/0055023 A1 | 3/2005 | Sohngen et al. |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0233100 A1 | 10/2007 | Metzinger |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |

(56) References Cited

U.S. PATENT DOCUMENTS

| | | |
|---|---|---|
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094306 A1 | 4/2010 | Chang et al. |
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0209265 A1 | 8/2012 | Pool |
| 2012/0209269 A1* | 8/2012 | Pool ............ A61B 50/34 606/63 |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0250674 A1* | 9/2014 | Pool ............ A61B 90/06 29/525.11 |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0057663 A1* | 2/2015 | Kinmon ............ A61B 17/7241 606/64 |
| 2015/0105782 A1 | 4/2015 | D'Lima et al. |
| 2015/0105824 A1 | 4/2015 | Moskowitz et al. |
| 2015/0223854 A1 | 8/2015 | Skinlo |
| 2015/0313745 A1 | 11/2015 | Cheng |
| 2017/0100173 A1* | 4/2017 | Abdelgawad ...... A61B 17/8057 |

FOREIGN PATENT DOCUMENTS

| | | |
|---|---|---|
| CN | 101040807 A | 9/2007 |
| CN | 202218907 U | 5/2012 |
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 7/2012 |
| JP | H0956736 | 3/1997 |
| JP | 2002500063 A | 1/2002 |
| WO | WO1998044858 A1 | 1/2002 |
| WO | WO1999051160 A1 | 1/2002 |
| WO | WO2001024697 A1 | 1/2002 |
| WO | WO2001045485 A3 | 1/2002 |
| WO | WO2001045487 A2 | 1/2002 |
| WO | WO2001067973 A2 | 1/2002 |
| WO | WO2001078614 A1 | 1/2002 |
| WO | WO2007015239 A3 | 1/2008 |
| WO | WO2007013059 A3 | 4/2009 |
| WO | WO2011116158 A3 | 1/2012 |
| WO | WO2013119528 A1 | 8/2013 |
| WO | WO2014040013 A1 | 3/2014 |

(56) References Cited

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral mahotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

(56) References Cited

OTHER PUBLICATIONS

Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering..General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511 , p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 23 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

(56) References Cited

OTHER PUBLICATIONS

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

\* cited by examiner

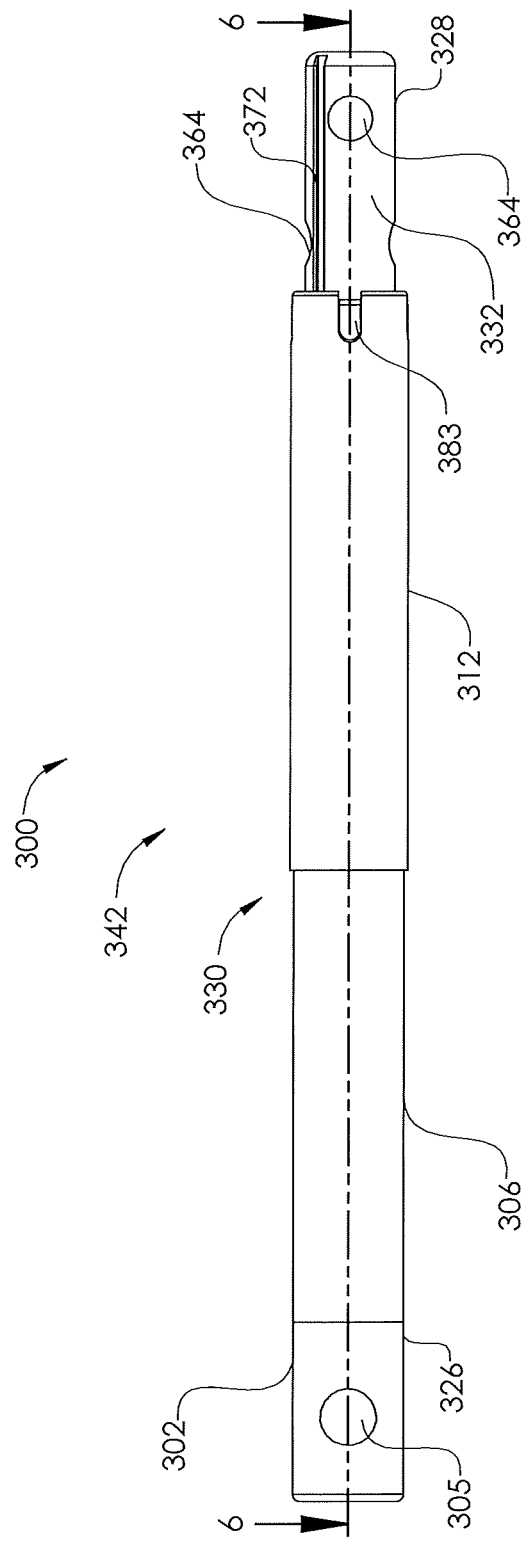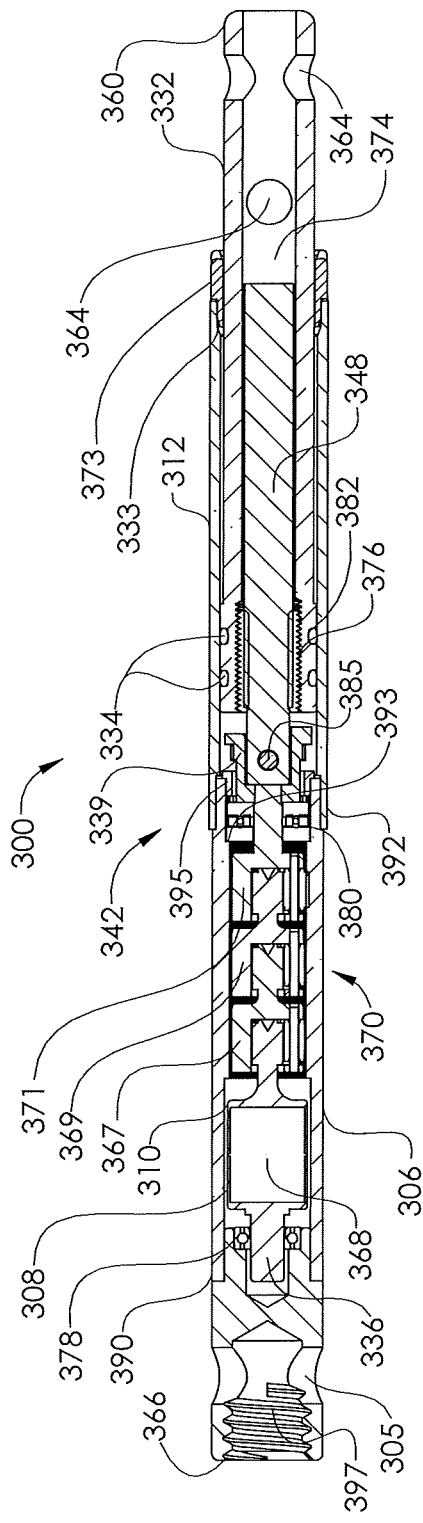

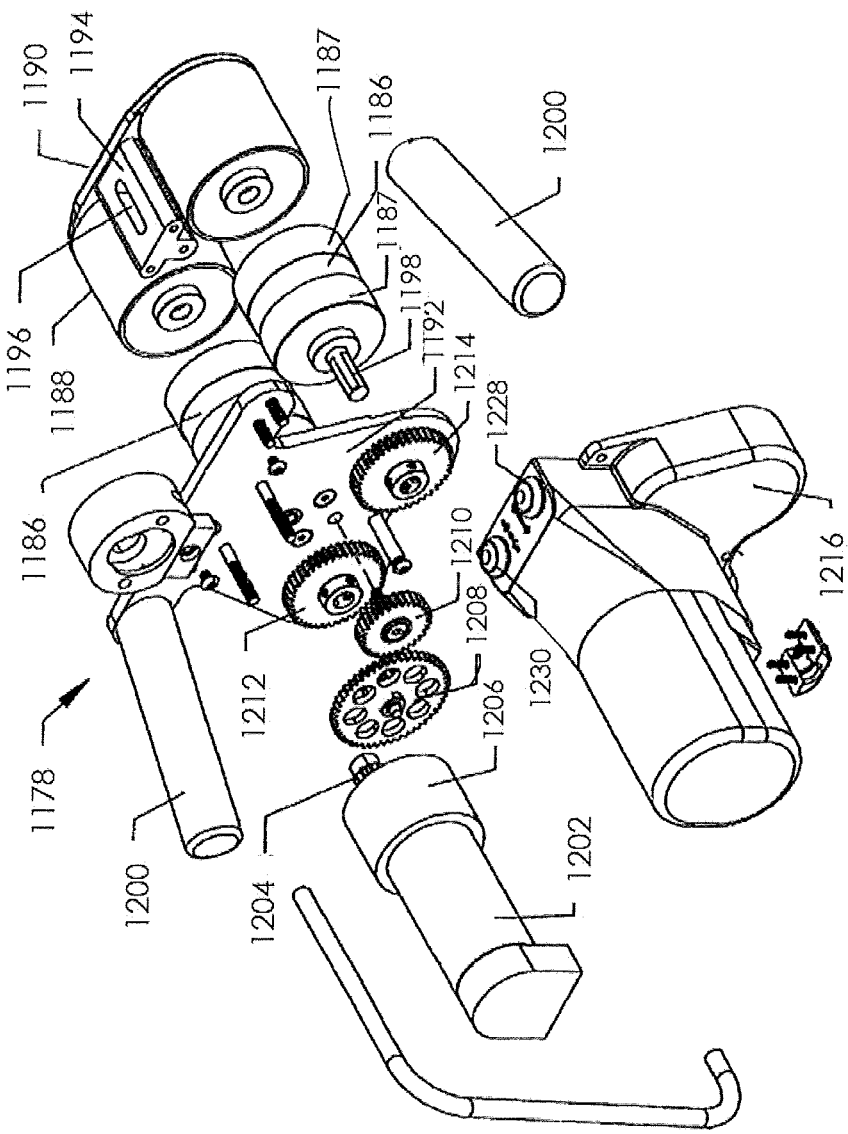

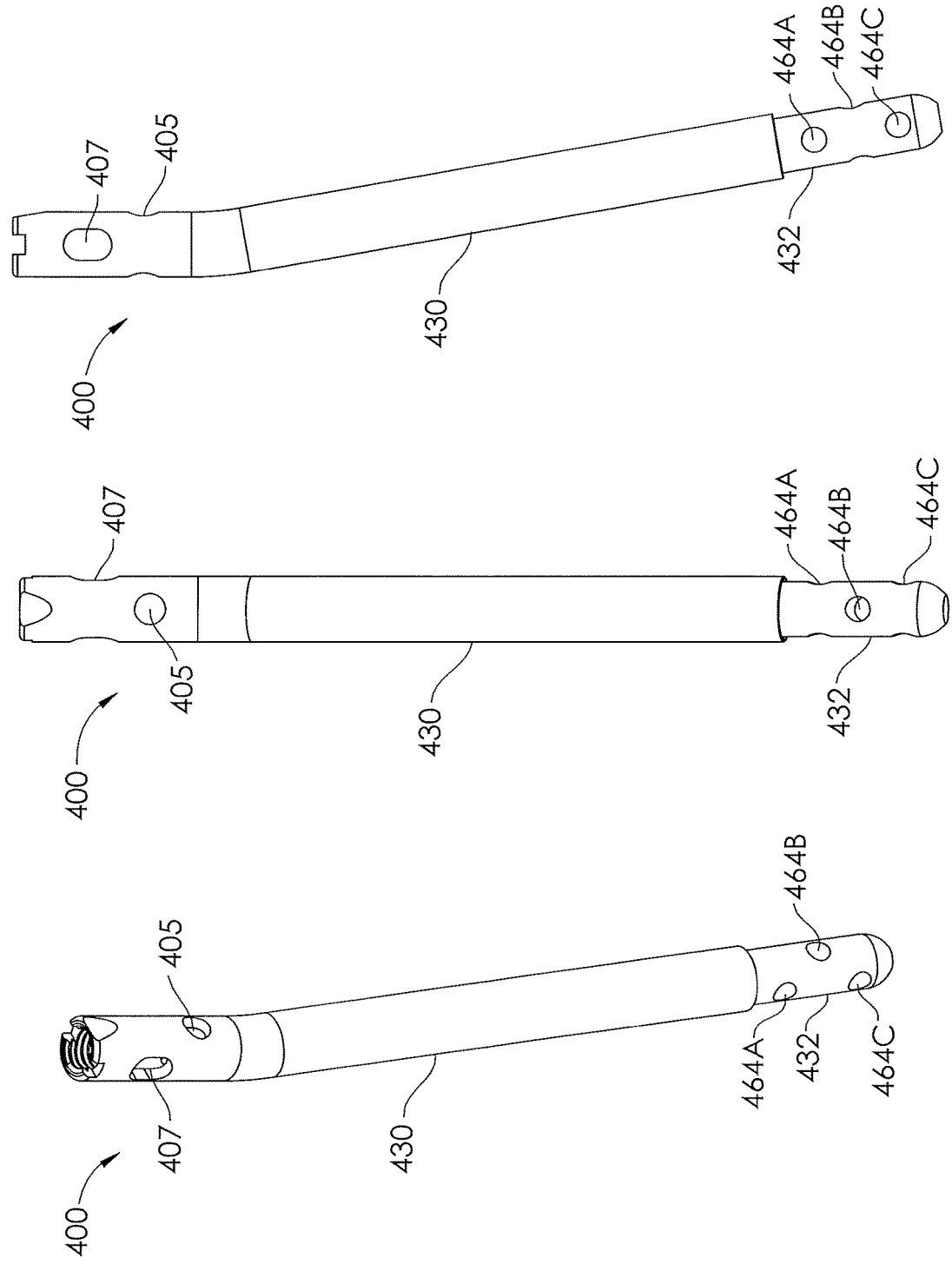

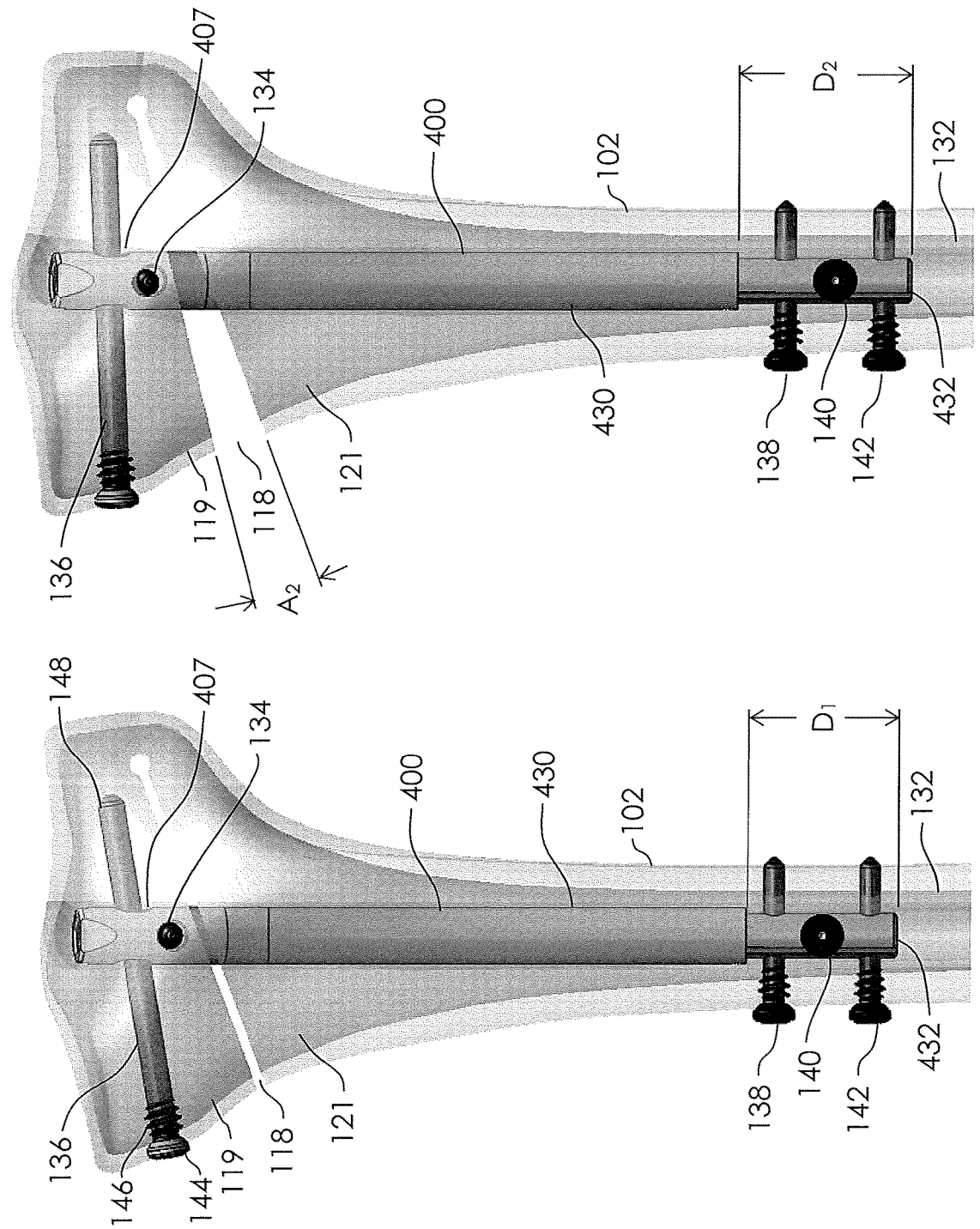

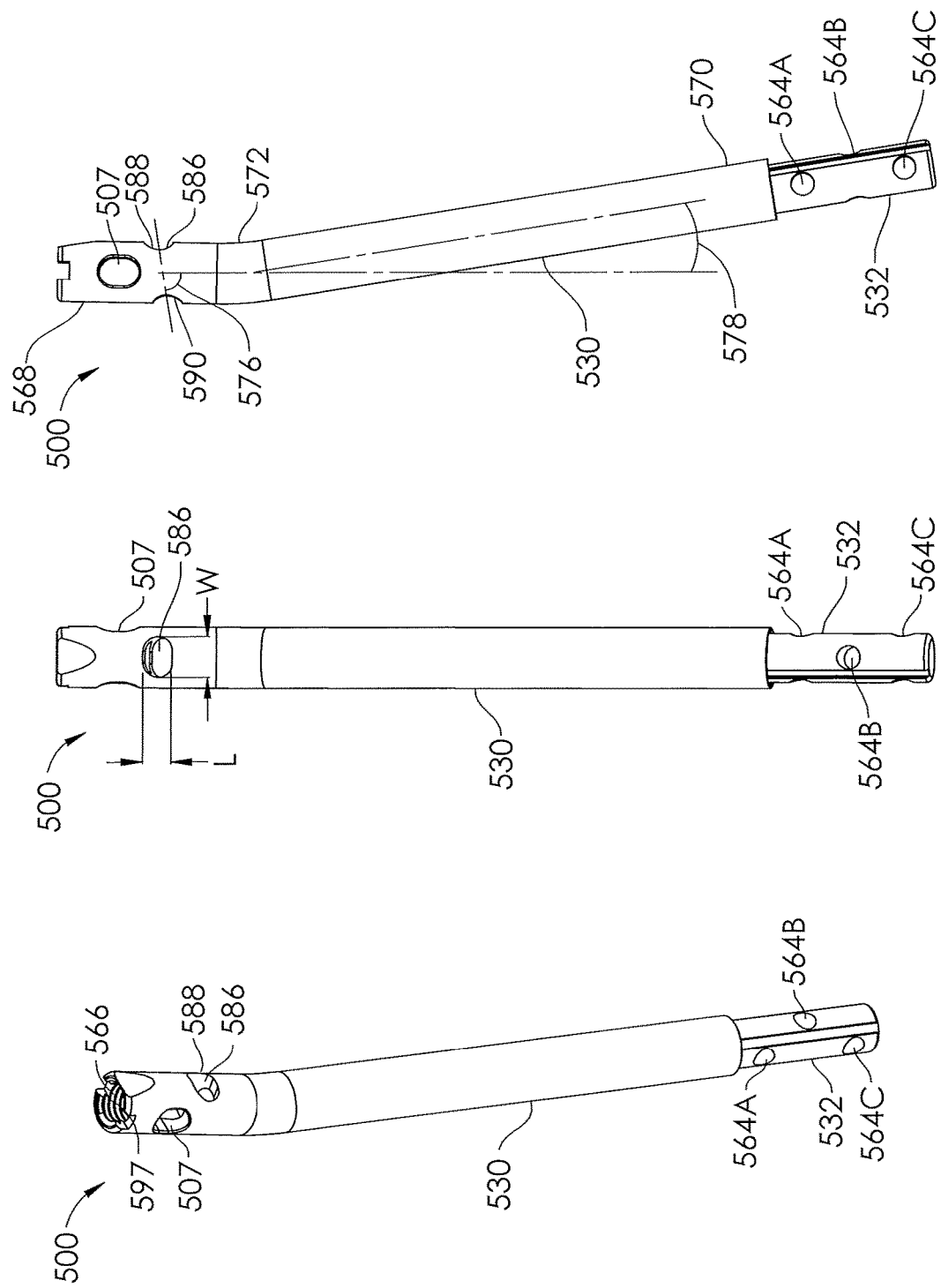

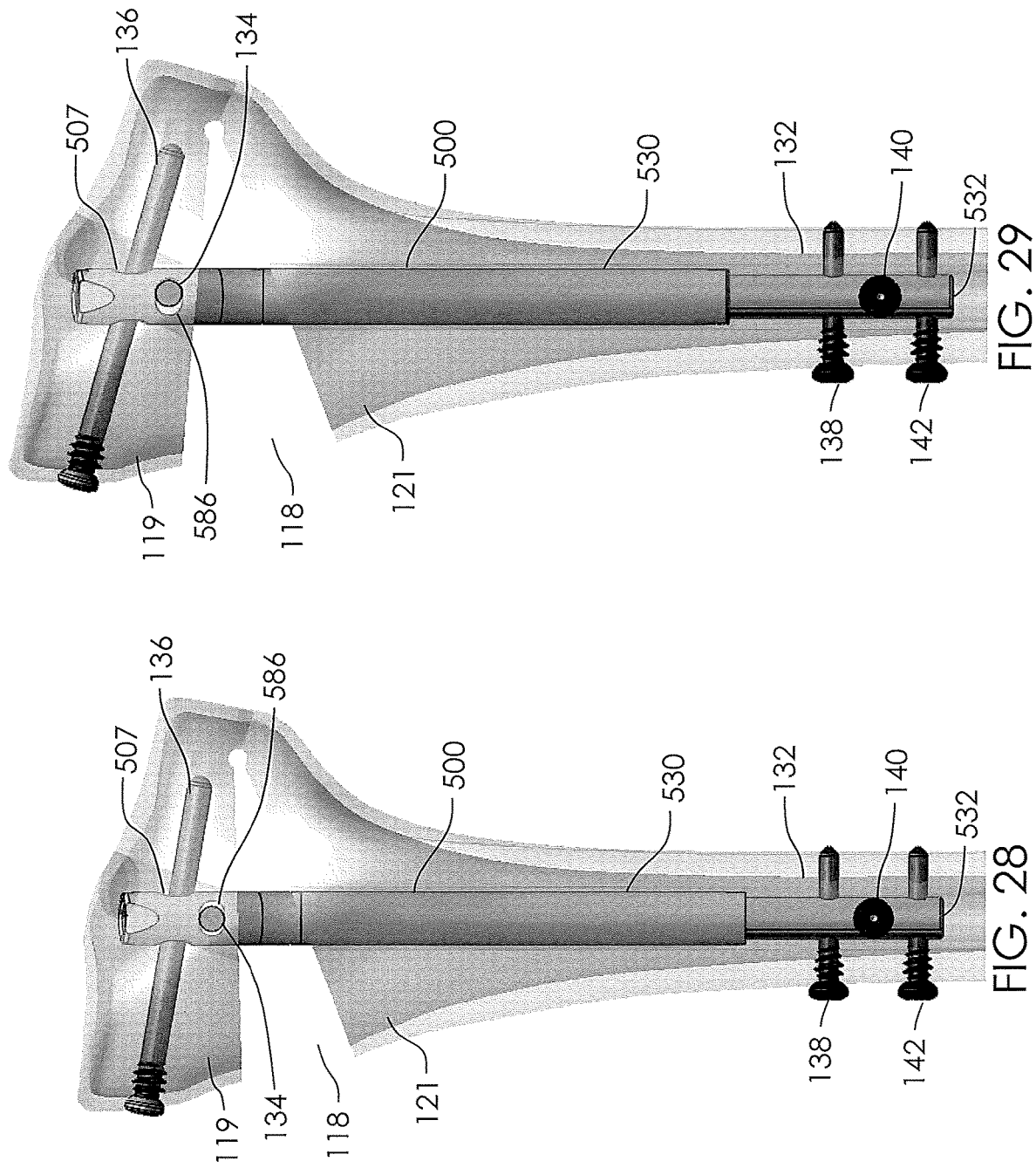

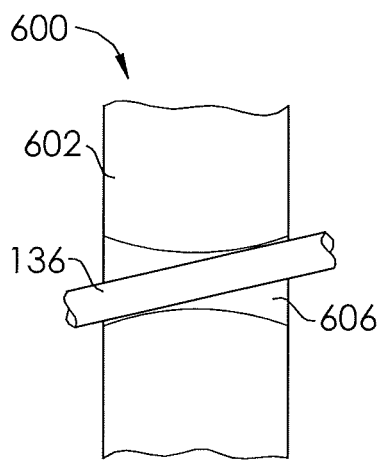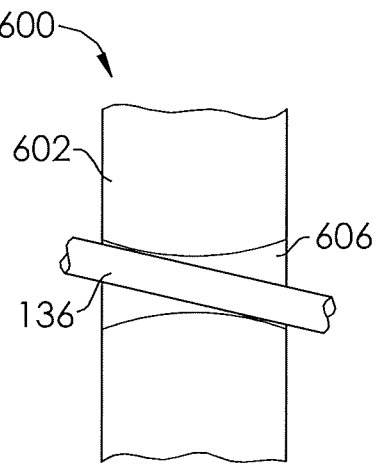
FIG. 33  FIG. 34
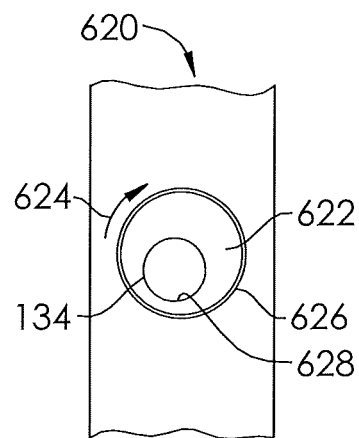
FIG. 35
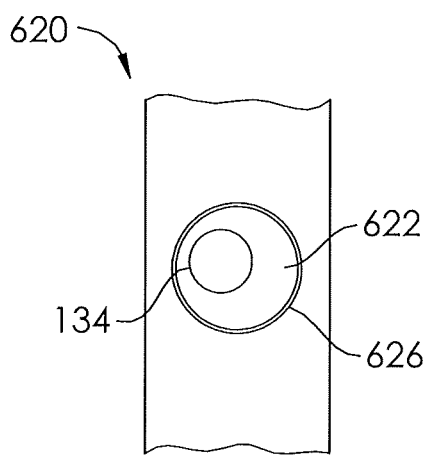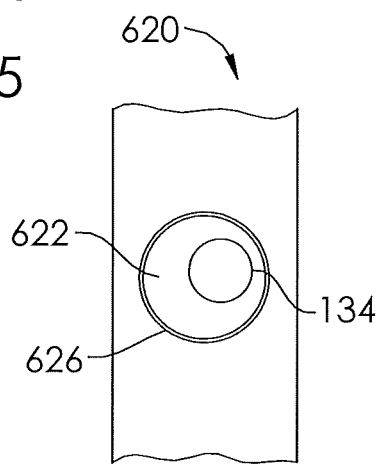
FIG. 36  FIG. 37

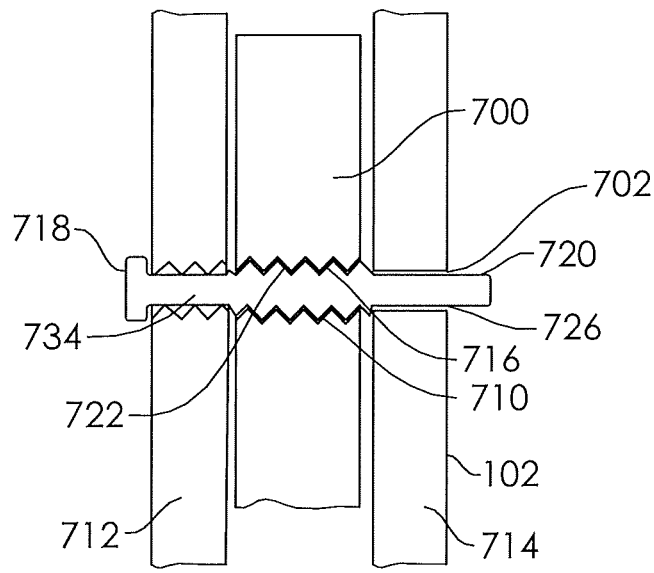
FIG. 40
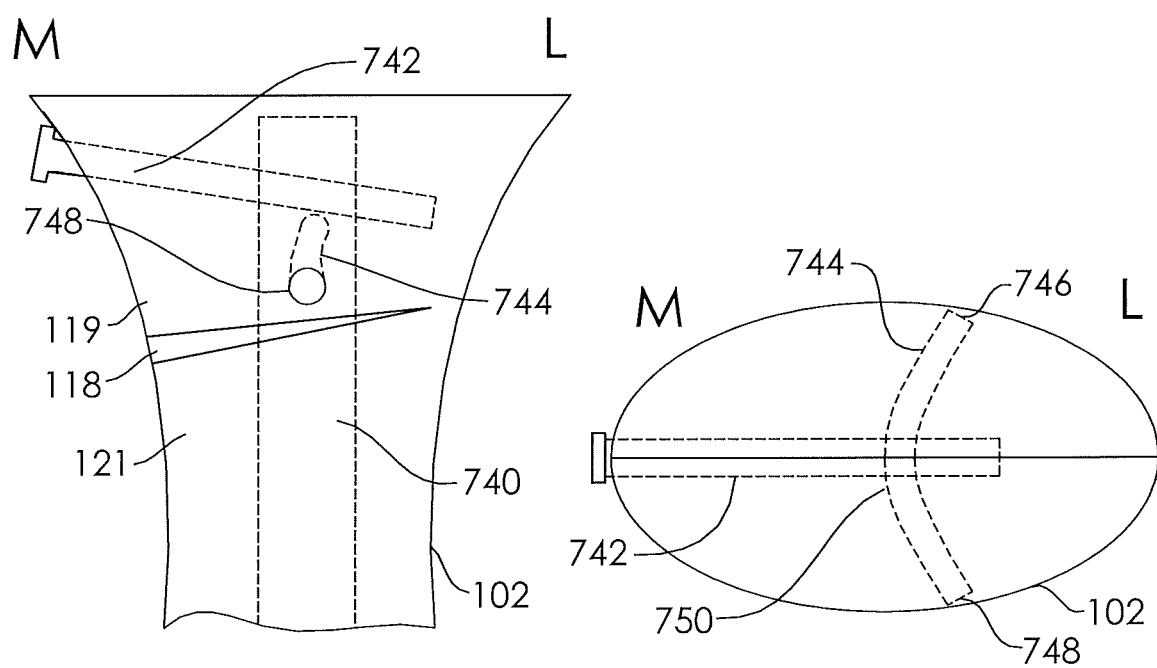
FIG. 41
FIG. 42

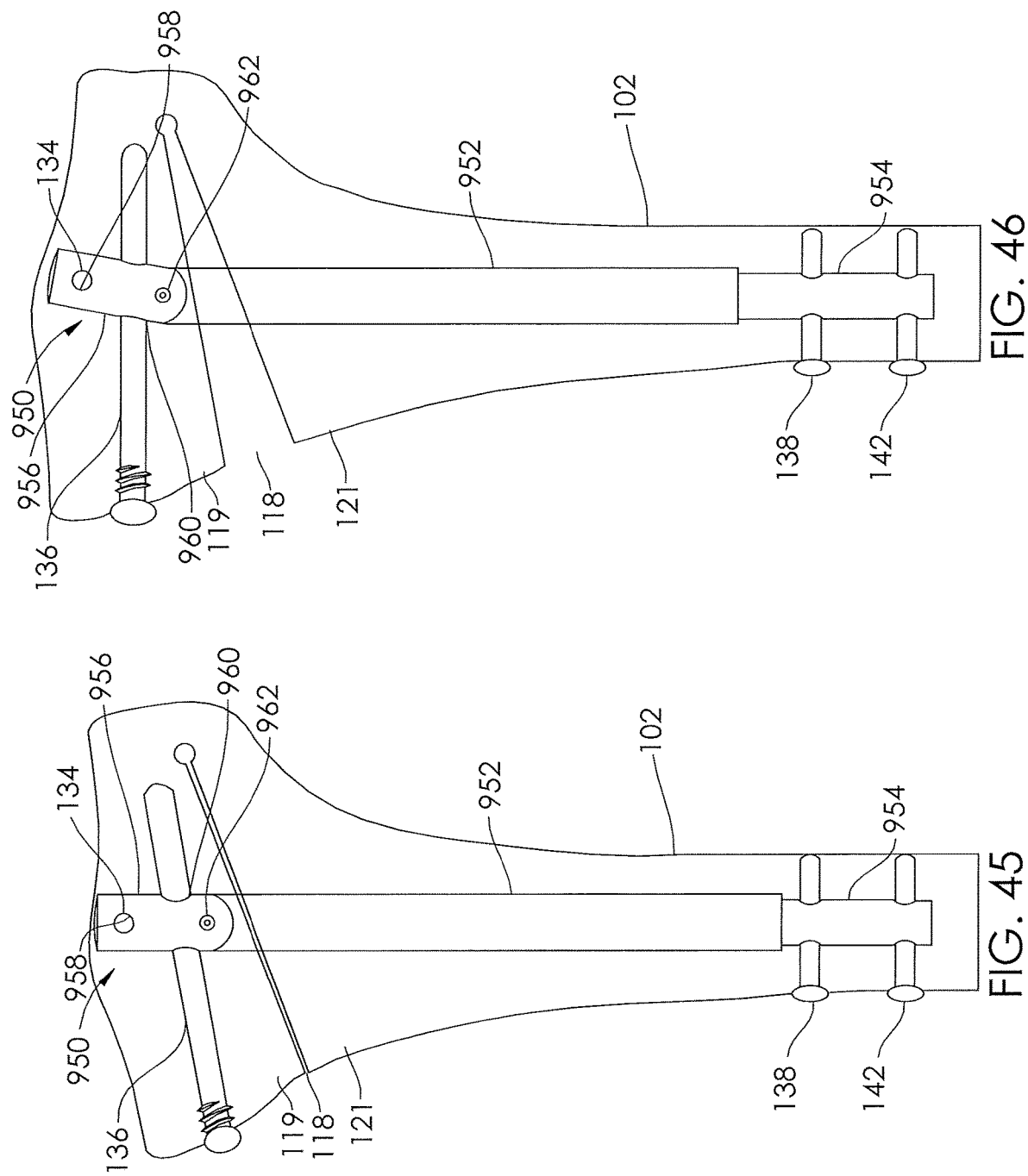

ADJUSTABLE DEVICES FOR TREATING ARTHRITIS OF THE KNEE

CROSS REFERENCE TO RELATED APPLICATIONS

Any and all applications for which a foreign or domestic priority claim is identified in the Application Data Sheet as filed with the present application are hereby incorporated by reference under 37 CFR 1.57.

BACKGROUND

Field of the Invention

The field of the invention generally relates to medical devices for treating knee osteoarthritis.

Description of the Related Art

Knee osteoarthritis is a degenerative disease of the knee joint that affects a large number of patients, particularly over the age of 40. The prevalence of this disease has increased significantly over the last several decades, attributed partially, but not completely, to the rising age of the population as well as the increase in obesity. The increase may also be due to the increase in highly active people within the population. Knee osteoarthritis is caused mainly by long term stresses on the joint that degrade the cartilage covering the articulating surfaces of the bones in the joint, including both the femur and tibia. Oftentimes, the problem becomes worse after a trauma event, but can also be a hereditary process. Symptoms may include pain, stiffness, reduced range of motion, swelling, deformity, and muscle weakness, among others. Osteoarthritis may implicate one or more of the three compartments of the knee: the medial compartment of the tibiofemoral joint, the lateral compartment of the tibiofemoral joint, and/or the patellofemoral joint. In severe cases, partial or total replacement of the knee may be performed to replace diseased portions with new weight bearing surfaces, typically made from implant grade plastics or metals. These operations can involve significant post-operative pain and generally require substantial physical therapy. The recovery period may last weeks or months. Several potential complications of this surgery exist, including deep venous thrombosis, loss of motion, infection, and bone fracture. After recovery, surgical patients who have received partial or total knee replacement must significantly reduce their activity, removing high energy and impact activities, including running and many other sports, completely from their lifestyle.

BRIEF DESCRIPTION OF THE DRAWINGS

FIG. 5 illustrates a non-invasively adjustable wedge osteotomy device.
FIG. 6 illustrates a cross-sectional view of the non-invasively adjustable wedge osteotomy device of FIG. 5 taken along line 6-6.
FIG. 9 illustrates an exploded view of the magnetic handpiece of the external adjustment device of FIG. 8.
FIGS. 10-12 illustrate various views of another embodiment of a non-invasively adjustable wedge osteotomy device.
FIG. 18 illustrates a non-invasively adjustable wedge osteotomy device within a tibia in a substantially non-adjusted state.
FIG. 19 illustrates a non-invasively adjustable wedge osteotomy device within a tibia in a first adjusted state.
FIGS. 23-25 illustrate various views of another embodiment of a non-invasively adjustable wedge osteotomy device.
FIGS. 27-29 illustrate the non-invasively adjustable wedge osteotomy device of FIG. 23 within a tibia in various states of adjustment.
FIGS. 33-34 illustrate a tapered or hourglass shaped anchor hole of a non-invasively adjustable wedge osteotomy device with an anchor in various positions.
FIGS. 35-37 illustrate a non-invasively adjustable wedge osteotomy device having an eccentric bearing in various positions.
FIG. 40 illustrates an internally threaded anchor hole of an embodiment of the non-invasively adjustable wedge osteotomy device of FIG. 38.
FIG. 41 illustrates a front view of a tibia implanted with an embodiment of a non-invasively adjustable wedge osteotomy device.
FIG. 42 illustrates a top view of the tibia of FIG. 41.
FIGS. 45-46 illustrate a front view of a tibia implanted with another embodiment of a non-invasively adjustable wedge osteotomy device in various states of distraction.

SUMMARY OF THE INVENTION

Figure 1:
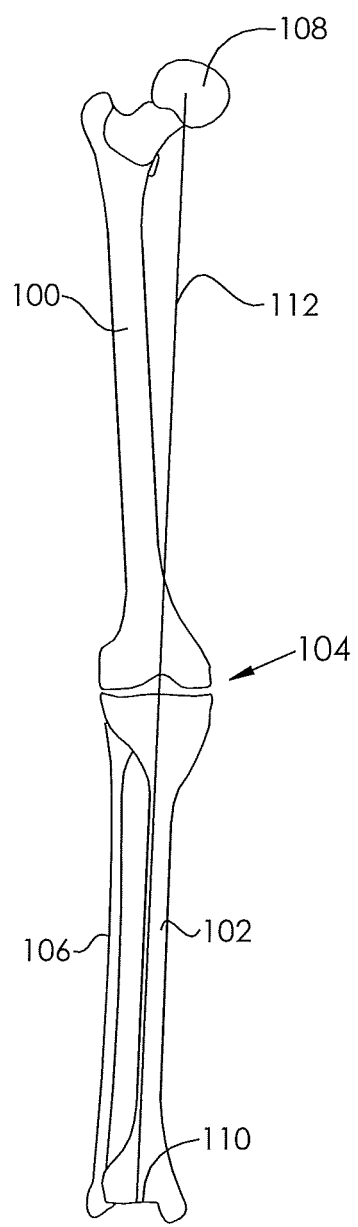
FIG. 1 illustrates a desirable alignment of a knee joint.

In a first embodiment, the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole and a second anchor hole, the first anchor hole configured to pass a first anchor for coupling the adjustable implant to a first portion of bone and the second anchor hole configured for to pass a second anchor for coupling the adjustable implant to the first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element configured to be remotely operable to telescopically displace the inner shaft in relation to the outer housing; and wherein the first anchor hole is configured to allow the first anchor to pivot in at least a first angular direction and the second anchor hole is configured to allow the second anchor to translate in at least a first translation direction.

In a second embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole, the first anchor hole configured to pass a first anchor for coupling the adjustable implant to a first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; and a driving element configured to be remotely operable to telescopically displace the inner shaft in relation to the outer housing; wherein the first anchor comprises a first end portion configured to slide within the slot and into cortical bone at a first side of the first portion of bone, a second end portion configured to slide within the slot and into cortical bone at a second side of the first portion of bone, and an intervening portion configured to reside within the first anchor hole.

In a third embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole, the first anchor hole configured to pass a first anchor for coupling the adjustable implant to a first portion of bone, wherein the first anchor hole is configured to allow the first anchor to pivot in at least a first angular direction, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element configured to be remotely operable to telescopically displace the inner shaft in relation to the outer housing; and wherein the at least one of the outer housing and inner shaft additionally includes two engagement portions configured to rotatably engage a curved anchor.

In a fourth embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one of the outer housing and inner shaft associated with a first anchor hole, the first anchor hole configured to pass a first anchor for coupling the adjustable implant to a first portion of bone wherein the first anchor hole is configured to allow the first anchor to pivot in at least a first angular direction, the inner shaft configured to couple to a second portion of bone that is separated or separable from the first portion of bone; and a driving element configured to rotate a screw threadingly coupled to a nut, the nut comprising an extreme portion configured to contact a location on the first anchor when the first anchor is within the first anchor hole, such that remote actuation of the drive element causes the screw to rotate and to longitudinally displace the nut, thus causing the first anchor to pivot in the first rotational direction.

In a fifth embodiment the disclosure provides a system for changing the angle of a bone of a subject, comprising a non-invasively adjustable implant configured to be placed inside a longitudinal cavity within the bone and comprising an outer housing and an inner shaft telescopically disposed in the outer housing, at least one end of the non-invasively adjustable implant associated with a first anchor hole, the first anchor hole configured to pass a first anchor for coupling the adjustable implant to a first portion of bone, the inner shaft configured to couple to a second portion of bone that is separated or separable from the first portion of bone, such that non-invasive elongation of the adjustable implant causes the inner shaft to extend from the outer housing and to move the first portion of bone and the second portion of bone apart angularly; a driving element configured to be remotely operable to telescopically displace the inner shaft in relation to the outer housing; wherein the at least one end of the non-invasively adjustable implant is rotatably coupled to at least one of the outer housing or the inner shaft.

DETAILED DESCRIPTION

In view of the ramifications of partial and/or total knee replacement surgery, it may be advantageous to intervene early in the progression of a patient's arthritis. In such cases, knee replacement surgery may be delayed or even precluded. Osteotomy surgeries may be performed on the femur or tibia to change the angle between the femur and tibia thereby adjusting the stresses on the different portions of the knee joint. In closed wedge or closing wedge osteotomy, an angled wedge of bone may be removed and the remaining surfaces fused together to create a new, improved bone angle. In open wedge osteotomy, a cut may be made in the bone and the edges of the cut opened to create a new angle.

Bone graft material may advantageously be used to fill in the new opened wedge-shaped space, and a plate may be attached to the bone with bone screws to provide additional structural support. However, obtaining a desired or correct angle during either a closed wedge or open wedge osteotomy, as described above, is almost always suboptimal. Furthermore, even if the resulting angle is approximately to that desired, there may be a subsequent loss of correction angle. Other potential complications that may be experienced when using these techniques include nonunion and material failure.

Figure 2:
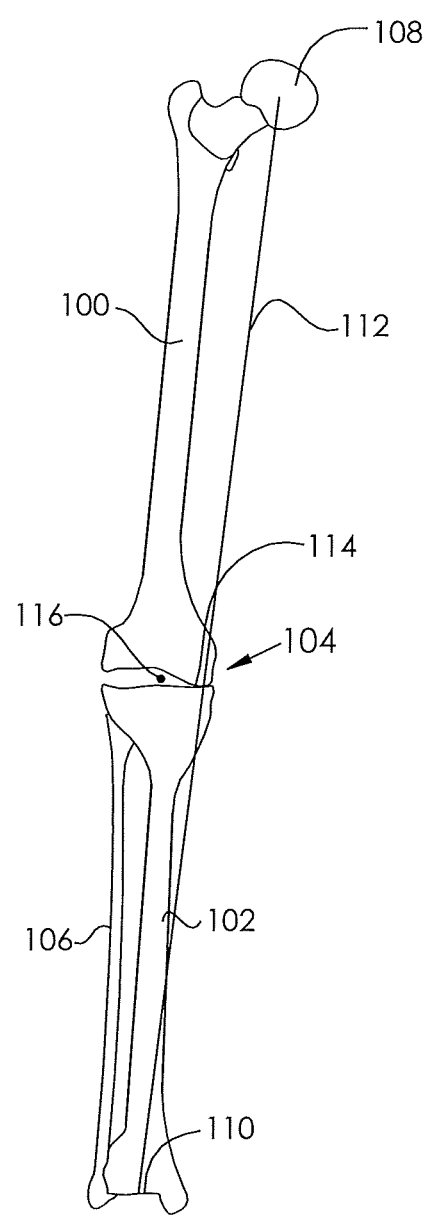
FIG. 2 illustrates a misaligned knee joint.

FIG. 1 illustrates a correct/healthy alignment of a femur 100, tibia 102, and knee joint 104. In such correct alignments, the a hip joint (at a femur head 108), knee joint 104, and ankle joint (at the midline of distal tibia 110) are generally disposed along a single line 112, known as the mechanical axis. A fibula 106 is shown alongside the tibia 102. By contrast to the knee joint 104 of FIG. 1, the knee joint 104 of FIG. 2 is shown in an arthritic state, in which the knee's medial compartment 114 (medial meaning situated in or disposed toward the middle or center) has been compromised, causing the line 112 to pass medially off the center of the knee joint 104.

Figure 4:
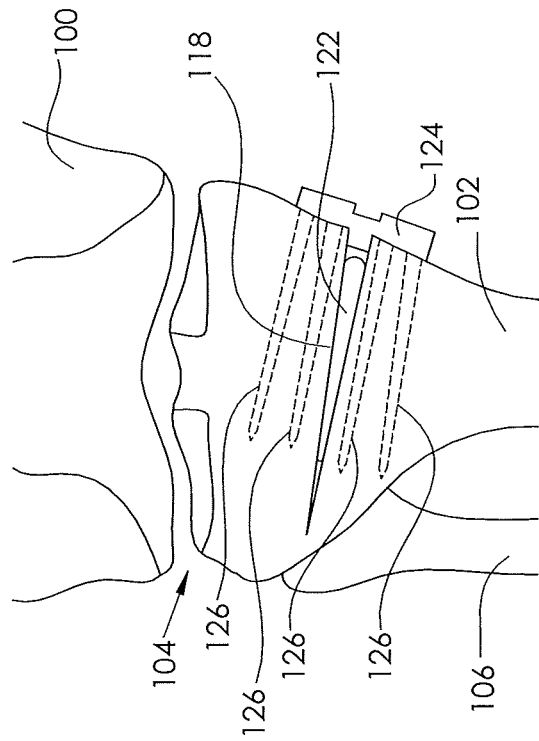
FIG. 4 illustrates an open wedge technique with bone graft inserted and a plate attached.
Figure 3:
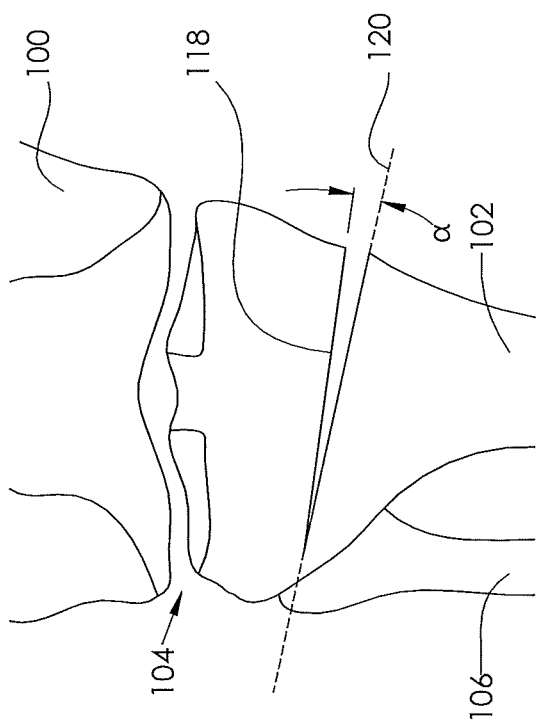
FIG. 3 illustrates an open wedge technique in a tibia.

FIG. 3 illustrates an open wedge osteotomy 118 formed by making a cut along a cut line 120, and opening a wedge angle α. FIG. 4 illustrates the final setting of this open wedge by the placement of bone graft material 122 within the open wedge osteotomy 118, and then placement of a plate 124, which is then secured to the tibia 102 with tibial screws 126. The increase in the wedge angle α can also be described as moving away from varus and/or moving towards valgus.

Figure 7:
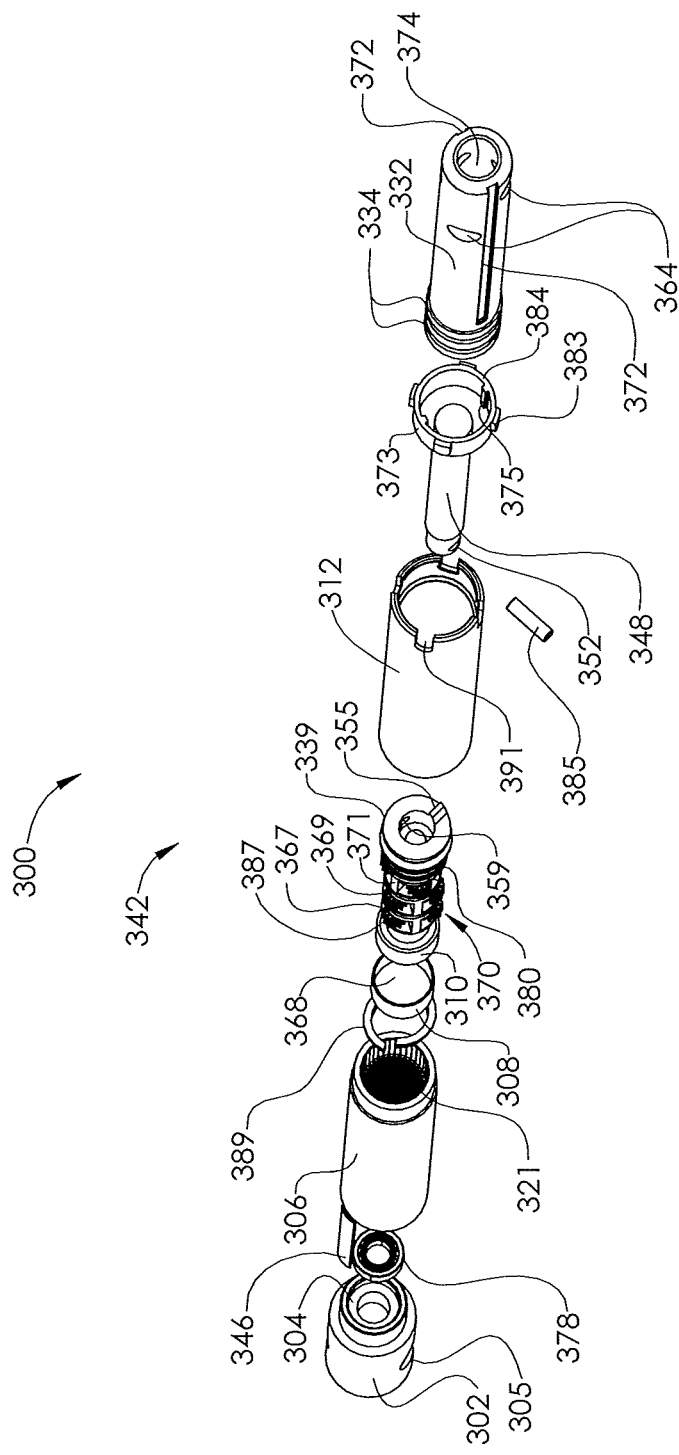
FIG. 7 illustrates an exploded view of the non-invasively adjustable wedge osteotomy device of FIG. 5.

FIGS. 5-7 illustrate a non-invasively adjustable wedge osteotomy device 300 comprising a magnetically adjustable actuator 342, and having a first end 326 and a second end 328. An inner shaft 332 having a cavity 374 is telescopically coupled to or within an outer housing 330 that comprises a distraction housing 312 and a gear housing 306. At least one proximal transverse hole 305 passes through an end cap 302 located at the first end 326 of the magnetically adjustable actuator 342. The at least one proximal transverse hole 305 allows passage of a bone screw, or other fixation device, therethrough to fix the adjustable wedge osteotomy device 300 to the bone in which it is implanted, e.g., the tibia 102. The end cap 302 may be sealably secured to the gear housing 306 by a circumferential weld joint 390. In some embodiments, the end cap 302 may be secured to the gear housing 306 by any appropriate method of fixation, such as friction, glues, epoxies, or any type of welding. In yet other embodiments, the end cap 302 and the gear housing 306 may be formed monolithically, or in one piece. A second weld joint 392 sealably secures the distraction housing 312 to the gear housing 306. In some embodiments, the distraction housing 312 may be secured to the gear housing 306 by any appropriate method of fixation, such as friction, glues, epoxies, or any type of welding. In yet other embodiments, the distraction housing 312 and the gear housing 306 may be formed monolithically, or in one piece. One or more distal transverse holes 364 pass through the inner shaft 332. The one or more distal transverse holes 364 allows passage of a bone screw, or other fixation device, therethrough to fix the adjustable wedge osteotomy device 300 to the bone in which it is implanted, e.g., the tibia 102. For example, the one or more distal transverse holes 364 and the at least one proximal transverse hole 305 allow passage of at least one locking screw. Some embodiments use only one distal transverse hole 364 and one proximal transverse hole 305 in order to better allow rotational play between the magnetically adjustable actuator 342 and the locking screws as the magnetically adjustable actuator 342 is adjusted.

In some embodiments, one or more longitudinal grooves 372 in the outer surface of the inner shaft 332 engage with protrusions 375 of an anti-rotation ring 373 (Shown in FIG. 7) to advantageously minimize or inhibit rotational movement between the inner shaft 332 and the distraction housing 312. The anti-rotation ring also engages undercuts 333 within end of the distraction housing 312 at a flat edge 384 of the anti-rotation ring 373. One or more guide fins 383 in the anti-rotation ring 373 can keep the anti-rotation ring 373 rotationally static within cuts 391 in the distraction housing 312.

The contents of the magnetically adjustable actuator 342 may advantageously be protected from bodily fluids. In some embodiments, the contents of the magnetically adjustable actuator 342 are sealed off from the body by one or more o-rings 334 that may reside between the inner shaft 332 and the distraction housing 312. For example, one or more circumferential grooves 382 in the outer surface of the inner shaft 332, for dynamically sealing along the inner surface of the distraction housing 312. The inner shaft 332 may be extended/retracted axially with respect to the outer housing 330, for example, by a lead screw 348 turned by a cylindrical radially poled magnet 368. The cylindrical radially poled magnet 368 is bonded within a first portion of a magnet housing 308 and a second portion of a magnet housing 310 and is rotatably held on one end by pin 336 and a radial bearing 378, which directly engages the counterbore 304 (shown in FIG. 7) of the end cap 302. The second magnet housing 310 is connected to or coupled to a first stage 367 of a planetary gear system 370.

In some embodiments, the planetary gear system 370 may have one stage, two stages, three stages, four stages or even five stages. In other embodiments, more than five stages may be included, if required. The embodiment of the planetary gear system 370 shown in FIG. 6 has three stages. Regardless of how many stages are included in the device, they may work generally according to the description provided below. The planet gears 387 of the three planetary gear system 370 turn within inner teeth 321 within the gear housing 306 (shown in FIG. 7). The first stage 367 outputs to a second stage 369, and the second stage 369 outputs to a third stage 371. The last or third stage 371 is coupled to the lead screw 348. In some embodiments, the last or third stage 371 is coupled to the lead screw 348 by a coupling that allows some degree of axial play between the third stage 371 and the lead screw 348, such as, for example, by a locking pin 385 that passes through holes 352 in both the output of the third stage 371 and in the lead screw 348. Alternatively, the third stage 371 may output directly to the lead screw 348. The lead screw 348 threadingly engages with a nut 376 that is bonded within the cavity 374 of the inner shaft 332. Each stage of the planetary gear system 370 incorporates a gear ratio. In some embodiments, the gear ratio may be 2:1, 3:1, 4:1, 5:1, or 6:1. In other embodiments, the gear ratio may be even higher than 6:1, if necessary. The overall gear ratio produced by the planetary gear system is equal to the each side of the gear ratio raised to the number of stages. For example, a three (3)-stage system having a gear ratio of 4:1, such as that shown in FIG. 6, has a final ratio of 4*4*4:1*1*1, or 64:1. A 64:1 gear ratio means that 64 turns of the cylindrical radially poled magnet 368 cause a single turn of the lead screw 348. In the same way, a two (2)-stage system having a gear ratio of 3:1 has a final ratio of 3*3:1*1, or 9:1. In some embodiments, the planetary gear system 370 includes stages with different gear ratios. For example, a three-stage planetary gear system 370 could include a first stage having a gear ratio of 4:1, a second stage having a gear ratio of 3:1, and a third stage having a ratio of 2:1: that system has a final ratio of 4*3*2:1*1*1, or 24:1. It may be desirable to include structural features in the housing to absorb axial loads on the cylindrical radially-poled magnet and/or the planetary gear system 370.

In some embodiments, one or more thrust bearings may be used to absorb axial loads. For example, thrust bearing 380 may be held loosely in the axial direction between ledges in the gear housing 306. The thrust bearing 380 is held between a ledge 393 in the gear housing 306 and an insert 395 at the end of the gear housing 306. The thrust bearing 380 advantageously protects the cylindrical radially poled magnet 368, the planetary gear system 370, the magnet housings 308 and 310, and the radial bearing 378 from unacceptably high compressive forces.

In some embodiments, a lead screw coupler 339 may be held to the lead screw 348 by the pin 385 passing through hole 359. The lead screw coupler 339 may include a ledge 355, which is similar to an opposing ledge (not shown) at the base of the lead screw 348. In these embodiments, when the inner shaft 332 is retracted to the minimum length, the ledge at the base of the lead screw 348 abuts the ledge 355 of the lead screw coupler, advantageously preventing the lead screw 348 from being jammed against the nut with too high of a torque.

A maintenance member 346, or magnetic brake, comprising a magnetic material, may be included (e.g., bonded) within the gear housing 306 adjacent to the cylindrical radially poled magnet 368. In such embodiments, the maintenance member 346 can attract a pole of the cylindrical radially poled magnet 368 to minimize unintentional rotation of the cylindrical radially poled magnet 368 (e.g., turning when not being adjusted by the external adjustment device 1180, such as during normal patient movement or activities). The maintenance member 346 may advantageously exert a lesser magnetic force on the cylindrical radially poled magnet 368 than the external adjustment device 1180. As such, the maintenance member holds the cylindrical radially poled magnet 368 substantially rotationally fixed most of the time (e.g., when not being adjusted during distraction/retraction). But, when the external adjustment device 1180 is used, the stronger forces of the external adjustment device 1180 overcome the force generated by the maintenance member 346 and turn the cylindrical radially poled magnet 368. In some embodiments, the maintenance member 346 is '400 series' stainless steel. In other embodiments, the maintenance member 346 can be any other appropriate magnetically permeable material.

The non-invasively adjustable wedge osteotomy device 300 has the capability to increase or decrease its length by extending the inner shaft 332 out from the distraction housing 312 and retracting the inner shaft 332 into the distraction housing 312, respectively. The non-invasively adjustable wedge osteotomy device 300 has a length of travel defined as the difference between its length when fully extended and its length when fully retracted. In some embodiments, the adjustable wedge osteotomy device 300 has a length of travel of less than about 30 mm, less than about 24 mm, less than about 18 mm, less than about 12 mm, and less than about 6 mm. In other embodiments, the non-invasively adjustable wedge osteotomy device 300 has a length of travel greater than 30 mm, or any other length of travel that is clinically meaningful. Interaction between the non-invasively adjustable wedge osteotomy device 300 and the magnetic handpiece 1178 of the external adjustment device 1180 that causes rotation of the cylindrical radially poled magnet 368 causes the inner shaft 332 to retract (depending on the direction of magnet rotation) into the distraction housing 312 thereby producing a compressive force, or causes the inner shaft 332 to extend (depending on the direction of magnet rotation) our from the distraction housing. The force that can be produced by the non-invasively adjustable wedge osteotomy device 300 is determined by a number of factors, including: size of cylindrical radially poled magnet 368, size of the maintenance member 346, magnetic force produced by the external adjustment device 1180 (determined by the size of the magnet(s) of the magnetic handpiece 1178), the distance between the magnetic handpiece 1178 and the cylindrical radially poled magnet 368, the number of gear stages, the gear ratio of each gear stage, internal frictional losses within the non-invasively adjustable wedge osteotomy device 300, etc. In some embodiments, the non-invasively adjustable wedge osteotomy device 300 in a clinical setting (i.e., implanted into an average patient) is capable of generating up to about 300 lbs., up to about 240 lbs., up to about 180 lbs., and up to about 120 lbs., or any other force that is clinically meaningful or necessary. In some embodiments, the magnetic handpiece 1178 of the external adjustment device 1180, placed so that its magnets 1186 are about one-half inch from the cylindrical radially poled magnet 368, can achieve a distraction force of about 240 pounds.

Many components of the non-invasively adjustable wedge osteotomy device may be made from Titanium, Titanium alloys (e.g., Titanium-6Al-4V), Cobalt Chromium, Stainless Steel, or other alloys. The diameter of the non-invasively adjustable wedge osteotomy device 300 is dictated by the size of the medullary canal 130 in the patient's tibia 102. While the medullary canal 130 may be enlarged through reaming or any other appropriate technique, it is generally desirable to select a non-invasively adjustable wedge osteotomy device 300 having a diameter approximately the same as or slightly smaller than the diameter of medullary canal 130. In some embodiments the non-invasively adjustable wedge osteotomy device 300 has a diameter of less than about 16 mm, less than about 14 mm, less than about 12 mm, less than about 10 mm, less than about 8 mm, or less than about 6 mm. In some embodiments, any other diameter that is clinically meaningful to a given patient may be used.

The non-invasively adjustable wedge osteotomy device 300 may be inserted by hand or may be attached to an insertion tool (for example a drill guide). In some embodiments, an interface 366 comprising an internal thread 397 is located in the end cap 302 for reversible engagement with male threads of an insertion tool. Alternatively, such engagement features may be located on the end 360 of the inner shaft 332. In other embodiments, a tether (e.g., a detachable tether) may be attached to either end of the non-invasively adjustable wedge osteotomy device 300, so that it may be easily removed if placed incorrectly.

Figure 8:
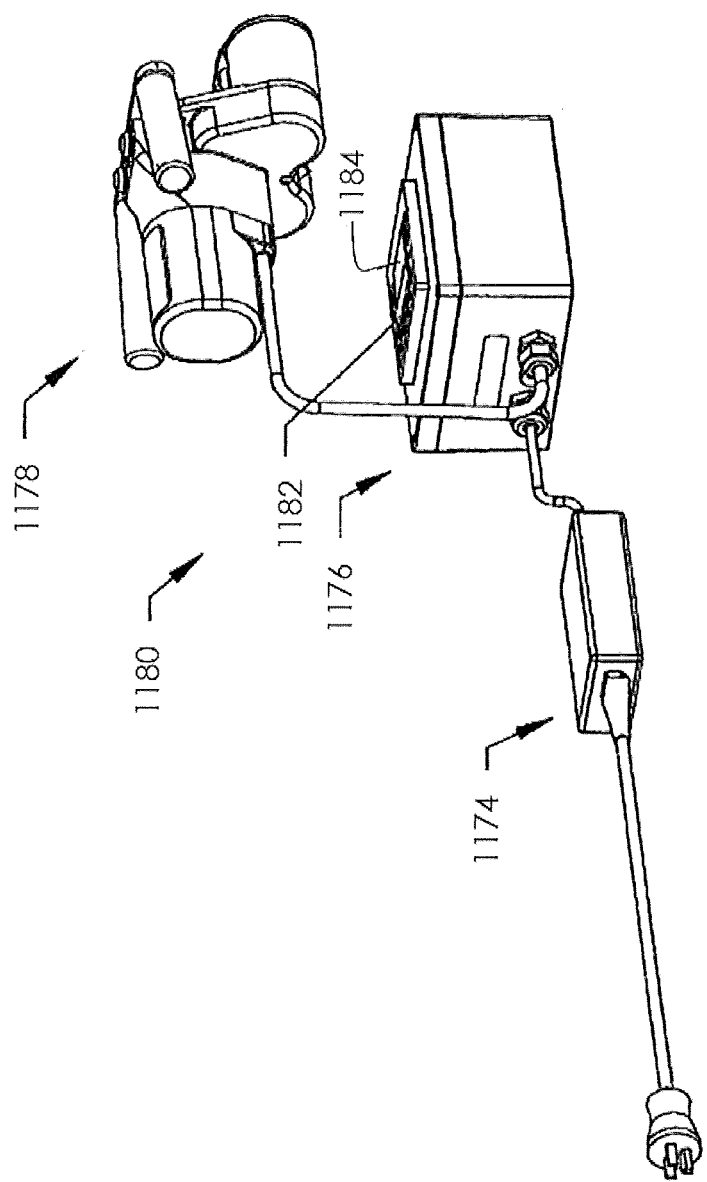
FIG. 8 illustrates an external adjustment device.

FIG. 8 illustrates an embodiment of an external adjustment device 1180 that is used to non-invasively adjust the devices and systems described herein. As shown in FIG. 8, the external adjustment device 1180 may include a magnetic handpiece 1178, a control box 1176, and a power supply 1174. The control box 1176 may include a control panel 1182 having one or more controls (buttons, switches, or tactile feedback mechanisms (i.e., any feedback mechanism that can be sensed using the sense of touch, including, for example, heat, vibration, change in texture, etc.), motion, audio or light sensors) and a display 1184. The display 1184 may be visual, auditory, tactile, the like or some combination of the aforementioned features. The external adjustment device 1180 may contain software that allows input by/from the physician.

FIG. 9 shows a detail of an embodiment of the magnetic handpiece 1178 of the external adjustment device 1180. The magnetic handpiece 1178 may include a plurality of magnets 1186, including 6 magnets, 5 magnets, 4 magnets, 3 magnets, or 2 magnets. In some embodiments, the magnetic handpiece 1178 may have only a single magnet. The magnets 1186 may have any of a number of shapes, including, for example, ovoid, cylindrical, etc. FIG. 9 illustrates a magnetic handpiece 1178 that includes two (2) cylindrical magnets 1186. The magnets 1186 can be rare earth magnets (such as Neodymium-Iron-Boron), and can in some embodiments be radially poled. In some embodiments, the magnets 1186 have 2 poles, 4 poles, or 6 poles. In other embodiments, the magnets 1186 have more than 6 poles. The magnets 1186 may be bonded or otherwise secured within magnetic cups 1187. The magnetic cups 1187 each includes a shaft 1198 that is attached to a first magnet gear 1212 and a second magnet gear 1214. The orientation of the poles of each the two magnets 1186 may be generally fixed with respect to each other. For example, the poles may be rotationally locked to one another using a gearing system, which may include a center gear 1210 that meshes with both first magnet gear 1212 and second magnet gear 1214. In some embodiments, the north pole of one of the magnets 1186 turns synchronously with the south pole of the other magnet 1186, at matching clock positions throughout a complete rotation. That configuration provides an improved torque delivery, for example, to radially poled cylindrical magnet 368. Examples of various external adjustment devices that may be used to adjust the various non-invasively adjustable wedge osteotomy devices disclosed herein are described in U.S. Pat. No. 8,382,756, and U.S. patent application Ser. No. 13/172,598, the entirety of which is incorporated by reference herein.

The components of the magnetic handpiece 1178 may be held together between a magnet plate 1190 and a front plate 1192. Components of the magnetic handpiece 1178 may be protected by a cover 1216. The magnets 1186 rotate within a static magnet cover 1188, so that the magnetic handpiece 1178 may be rested directly on the patient without imparting any motion to the external surfaces of the patient (e.g., rubbing against or pulling at the skin of the patient). Prior to use, such as activating a noninvasively adjustable medical device, an operator places the magnetic handpiece 1178 on the patient near the implantation location of the radially poled cylindrical magnet 368. In some embodiments, a magnet standoff 1194 that is interposed between the two magnets 1186 contains a viewing window 1196, to aid in placement of the magnetic handpiece 1178 on the patient. For instance, a mark made on the patient's skin at the appropriate location may be seen through the viewing window 1196 and used to align the magnetic handpiece 1178. To perform a distraction, an operator may hold the magnetic handpiece 1178 by its handles 1200 and depress a distract switch 1228, thereby causing motor 1202 to drive in a first rotational direction. The motor 1202 may have a gear box 1206 which causes the rotational speed of an output gear 1204 to be different from the rotational speed of the motor 1202 (for example, a slower speed or a faster speed). In some embodiments, the gear box 1206 causes the rotational speed of an output gear 1204 to be the same as the rotational speed of the motor. The output gear 1204 then turns a reduction gear 1208 which meshes with center gear 1210, causing it to turn at a different rotational speed than the reduction gear 1208. The center gear 1210 meshes with both the first magnet gear 1212 and the second magnet gear 1214 turning them at the same rate. Depending on the portion of the body where the magnets 1186 of the magnetic handpiece 1178 are located, it may be desirable that the rotation rate of the magnets 1186 be controlled to minimize the induced current density imparted by magnets 1186 and radially poled cylindrical magnet 368 through the tissues and fluids of the body. For example, a magnet rotational speed of 60 revolutions per minute ("RPM") or less is contemplated, although other speeds may be used, such as 35 RPM, or less. At any time, the distraction may be lessened by depressing the retract switch 1230, which can be desirable if the patient feels significant pain, or numbness in the area in which the noninvasively adjustable device has been implanted.

FIGS. 10-12 illustrate a non-invasively adjustable wedge osteotomy device 400 configured for maximizing the amount of potential increase of a wedge angle α. As explained with respect to other embodiments (e.g., the non-invasively adjustable wedge osteotomy device 300), an inner shaft 432 is configured to telescopically displace from an outer housing 430, such that the length of the non-invasively adjustable wedge osteotomy device 400 may be increased or decreased. The internal components of the non-invasively adjustable wedge osteotomy device 400 may be configured as is described with respect to other embodiments of the non-invasively adjustable wedge osteotomy device that are disclosed herein. The inner shaft 432 can include one or more transverse holes through which bone anchors or screws can be passed to anchor the device. Such transverse holes may be at any angle with respect to the vertical, and may be at any angle with respect to the horizontal. Desirably, when there is more than one transverse hole, the holes should, ideally, not intersect. In some embodiments, the inner shaft 432 includes three transverse holes 464A, 464B, and 464C for placement of bone screws. In some embodiments, the transverse hole 464B is generally at a 90° angle in relation to each of transverse holes 464A and 464C, which are approximately parallel to each other. Like the inner shaft 432, the outer housing 430 can include one or more transverse holes through which bone anchors or screws can be passed to anchor the device. In some embodiments, the outer housing 430 includes a first transverse hole 405 and a second, slotted transverse hole 407. The first transverse hole 405 may generally be at a 90° angle in relation to the second, slotted transverse hole 407. In some embodiments, the first transverse hole 405 is configured to extend in a generally lateral to medial direction when the non-invasively adjustable wedge osteotomy device 400 is placed within the tibia 102 (lateral meaning situated in or disposed toward the side or sides). In some embodiments, the second, slotted transverse hole 407 is configured to extend in a generally anterior to posterior direction when the non-invasively adjustable wedge osteotomy device 400 is placed within the tibia 102.

Figure 14:
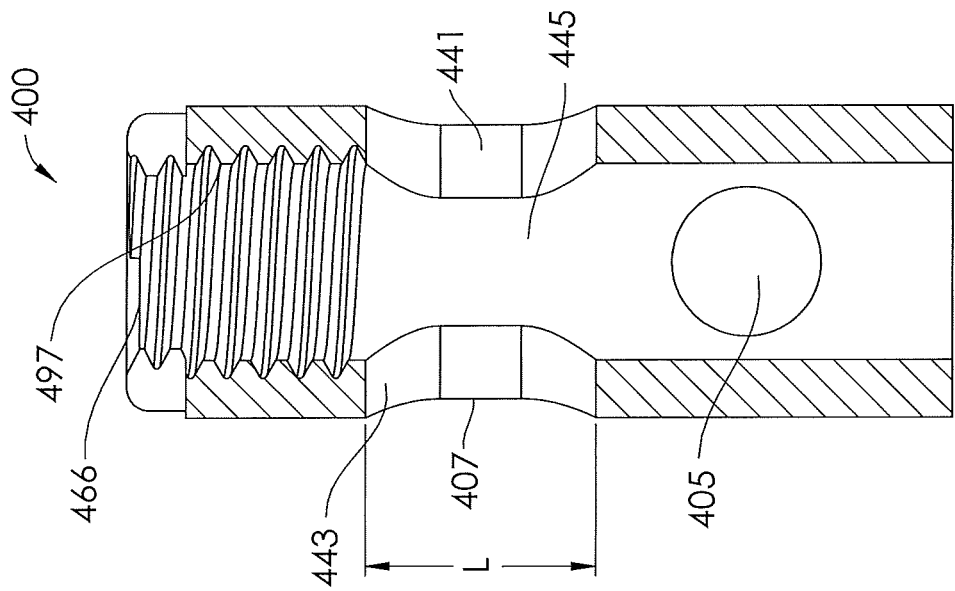
FIG. 14 illustrates a cross-sectional view of the non-invasively adjustable wedge osteotomy device of FIG. 13 taken along line 14-14.
Figure 13:
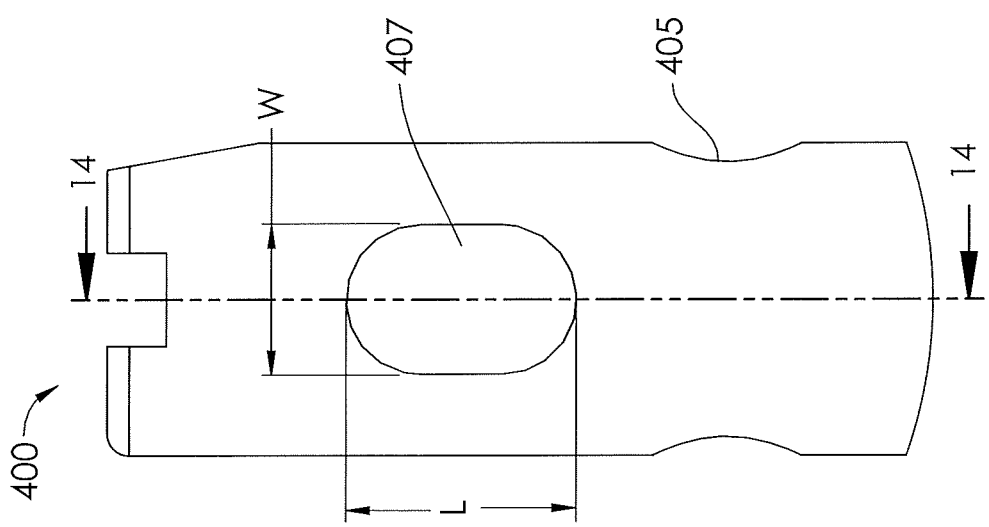
FIG. 13 illustrates an end of the non-invasively adjustable wedge osteotomy device of FIGS. 10-12.

The slotted transverse hole 407 generally extends through two walls 441, 443 of the non-invasively adjustable wedge osteotomy device 400 and through a center cavity 445 (shown in FIGS. 13-14). The slotted transverse hole 407 may have a generally oblong shape, with a length "L" and a width "W". The width W may be configured to be just slightly larger than a bone screw that is used to secure the non-invasively adjustable wedge osteotomy device 400 to a bone, such that the bone screw is able to pass through the slotted transverse hole 407. The length L may be chosen such that the bone screw is able to pivot or angularly displace within the slotted transverse hole 407 up to a desired maximum angulation within a plane (e.g., a plane substantially oriented as the coronal plane). In some embodiments, the ratio of length L to width W (L/W) is always greater than one (1), but is less than about 3, about 2.5, about 2, about 1.5, or about 1.2. By way of example, when the slotted transverse hole 407 is configured to accept a 5 mm bone screw, the width W may be about 5.05 mm-5.25 mm, about 5.1 mm-5.2 mm, or about 5.15 mm, and the length L may be about 6 mm-15 mm, about 7.5 mm-12.5 mm, or about 8 mm-10 mm. FIG. 14 also illustrates an interface 466 having an internal thread 497, which may be used for releasable detachment of an insertion tool.

Figure 51:
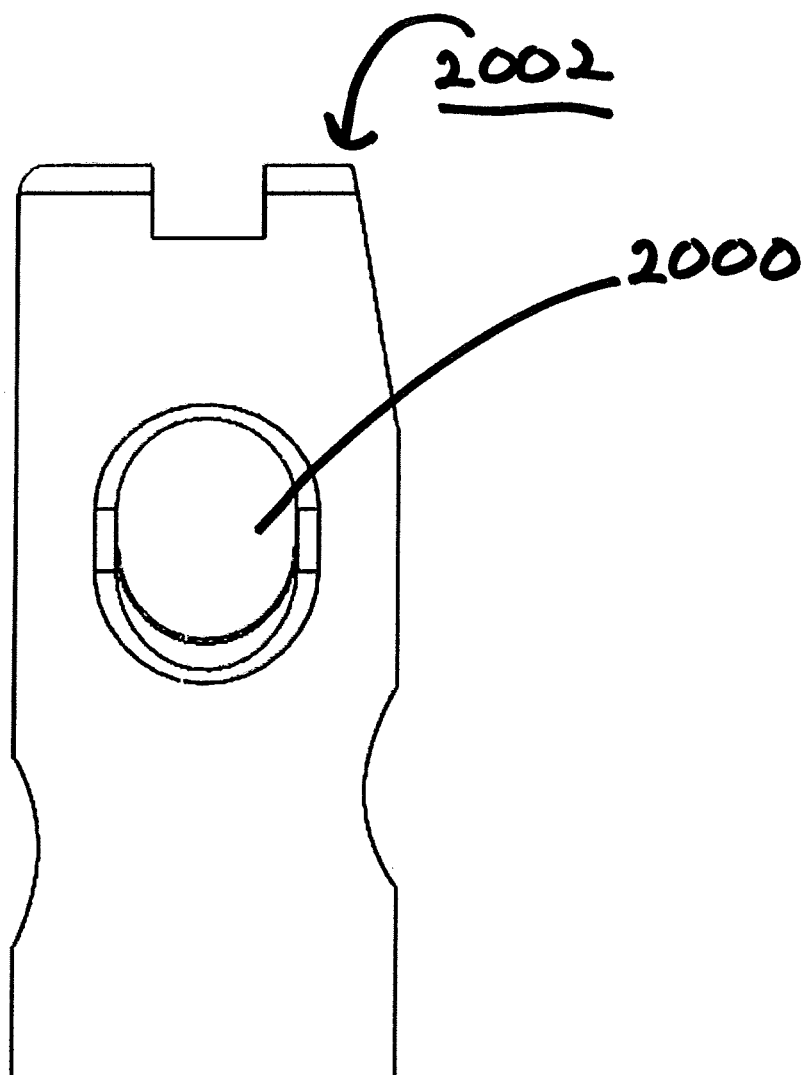
FIG. 51 illustrates a side view of one embodiment of the non-invasively adjustable wedge osteotomy device.
Figure 52:
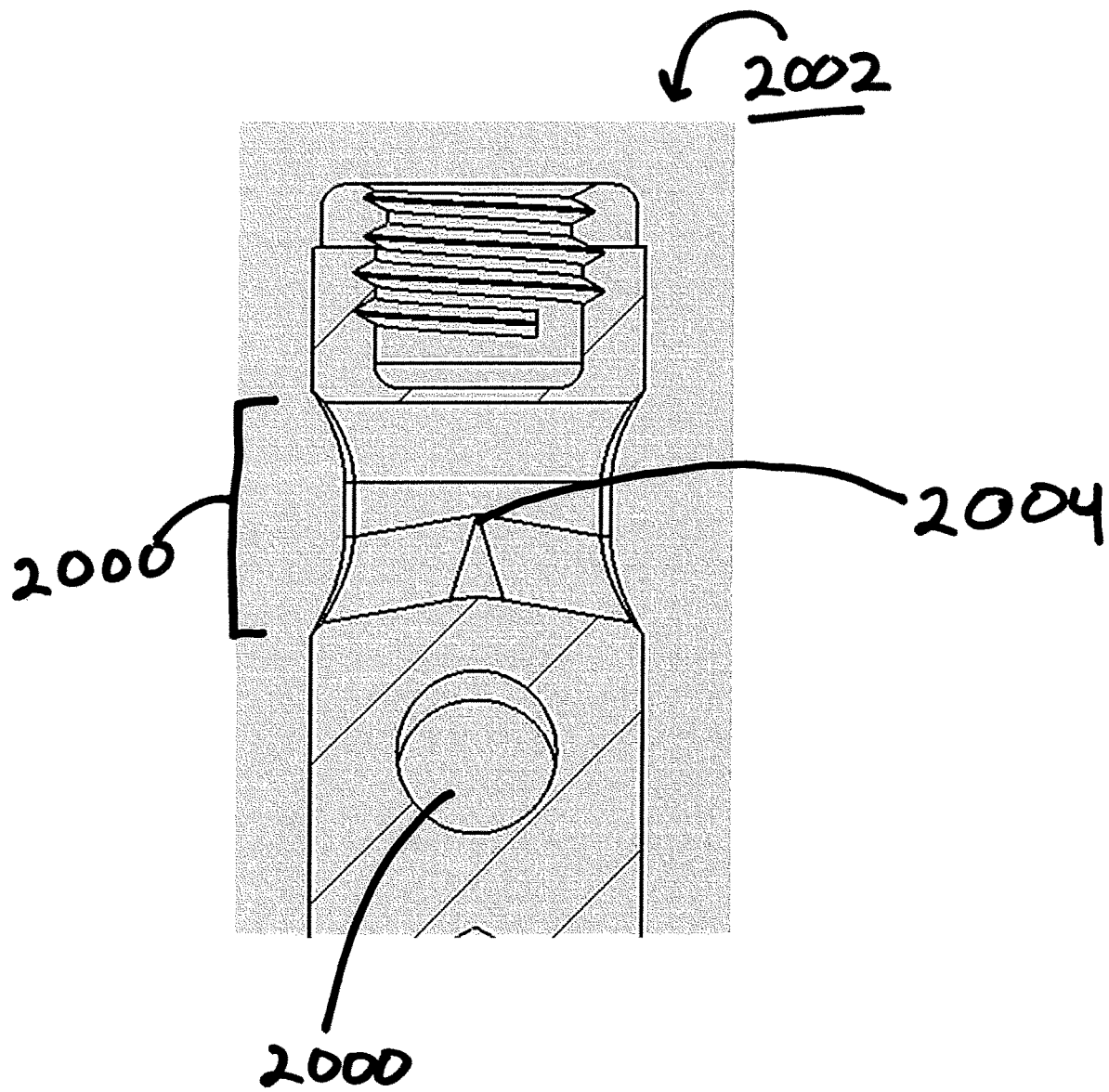
FIG. 52 illustrates a cross sectional view of the non-invasively adjustable wedge osteotomy device of FIG. 51.
Figure 53:
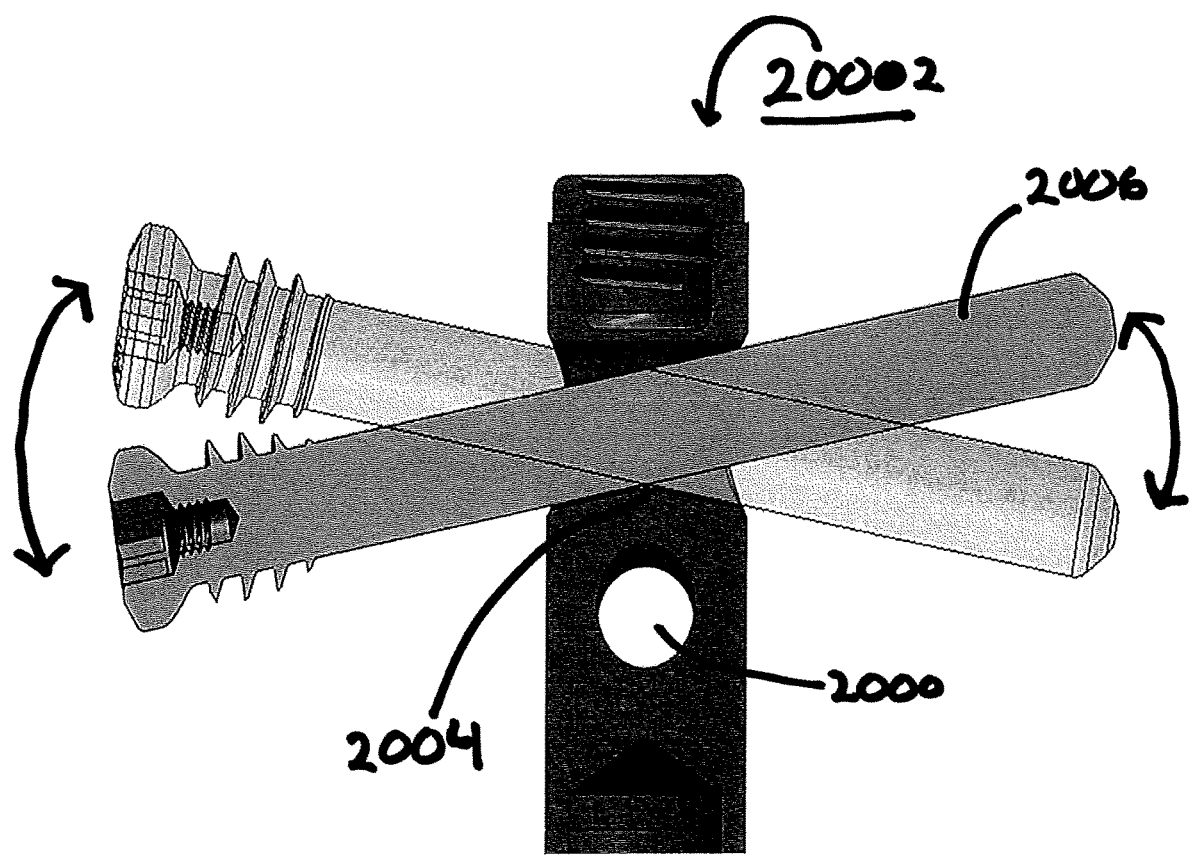
FIG. 53 illustrates yet another view of the non-invasively adjustable wedge osteotomy device of FIGS. 51 and 52.

In another embodiment illustrated by FIGS. 51-53 one or more of the transverse holes 2000 of the non-invasively adjustable wedge osteotomy device 2002 may have a raised portion 2004 substantially centrally located within the transverse holes 2000 upon which a bone anchors or screws 2006 can be passed to anchor the device. In one embodiment, the raised portion 2004 extends generally perpendicular to a longitudinal axis of the transverse holes 2000 such that the lower surface of the transverse hole has a decreasing slope from the raised portion to the exterior in each direction. The raised portion 2002 allows the bone anchors or screws 2006 to pivot providing (as shown by arrows in FIG. 53) greater bone anchor or screw 2006 angulation. The raised portion 2004 may be rounded or it may come to a discrete point within the one or more of the transverse holes 2000. In in embodiment, the bone anchors or screws 2006 may have up to about 40 degrees of movement from a first position to a second position and more specifically may have about 20 degrees of movement from the first position to the second position. The raised portion 2002 may provide an added advantage in that it allows the bone anchor or screw 2006 to achieve its full range of angulation while pivoting about a single point rather than two or more points.

Figure 15:
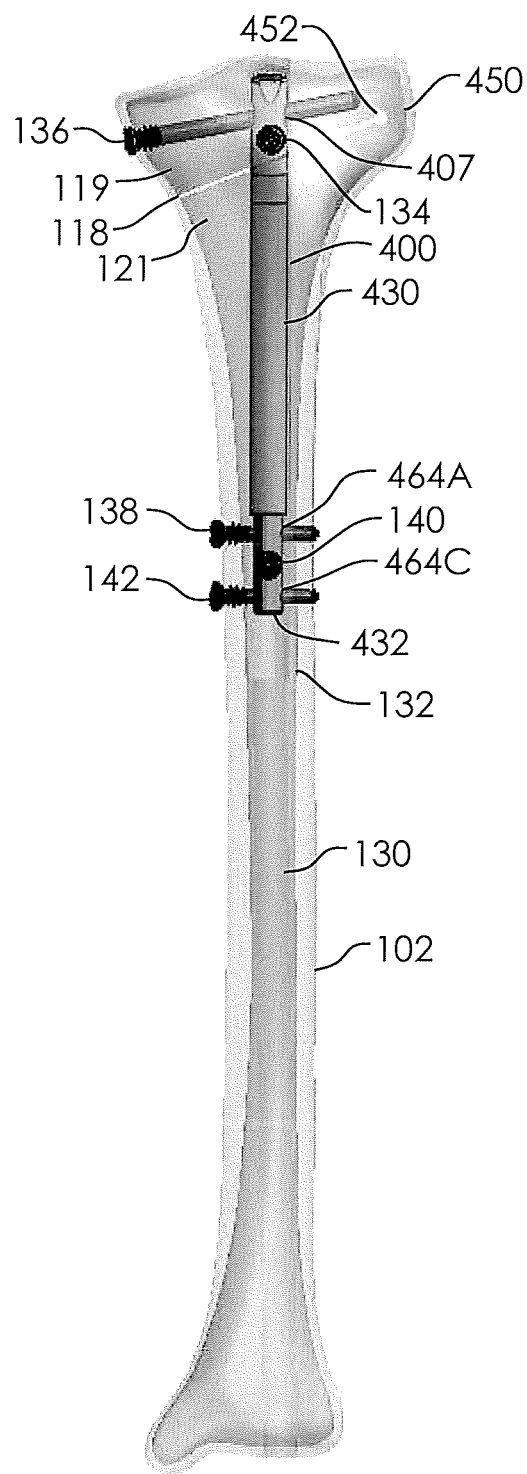
FIG. 15 illustrates a front view of a non-invasively adjustable wedge osteotomy device in place within a tibia.
Figure 16:
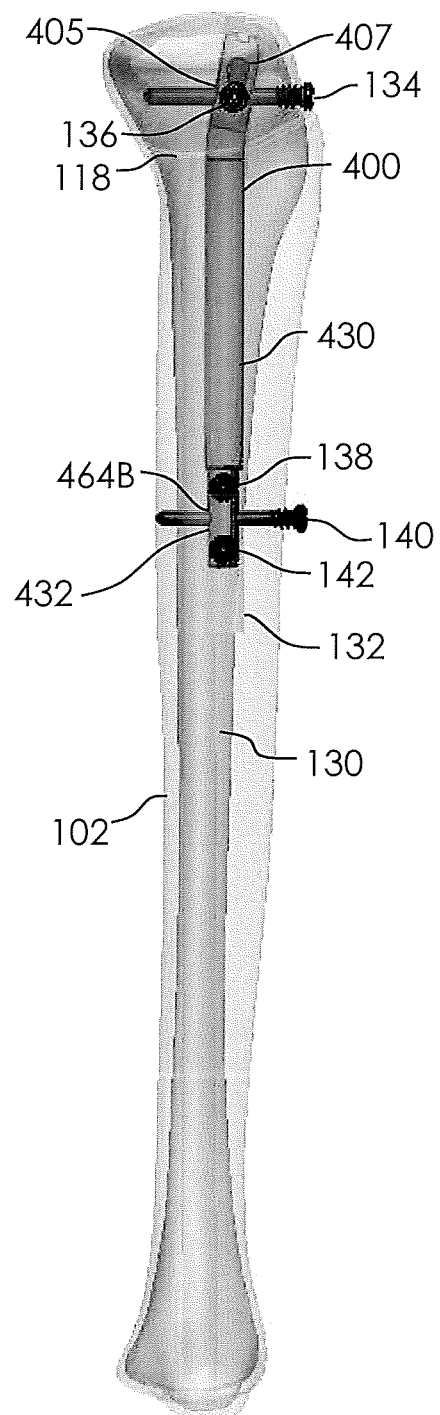
FIG. 16 illustrates a side view of a non-invasively adjustable wedge osteotomy device in place within a tibia.
Figure 17:
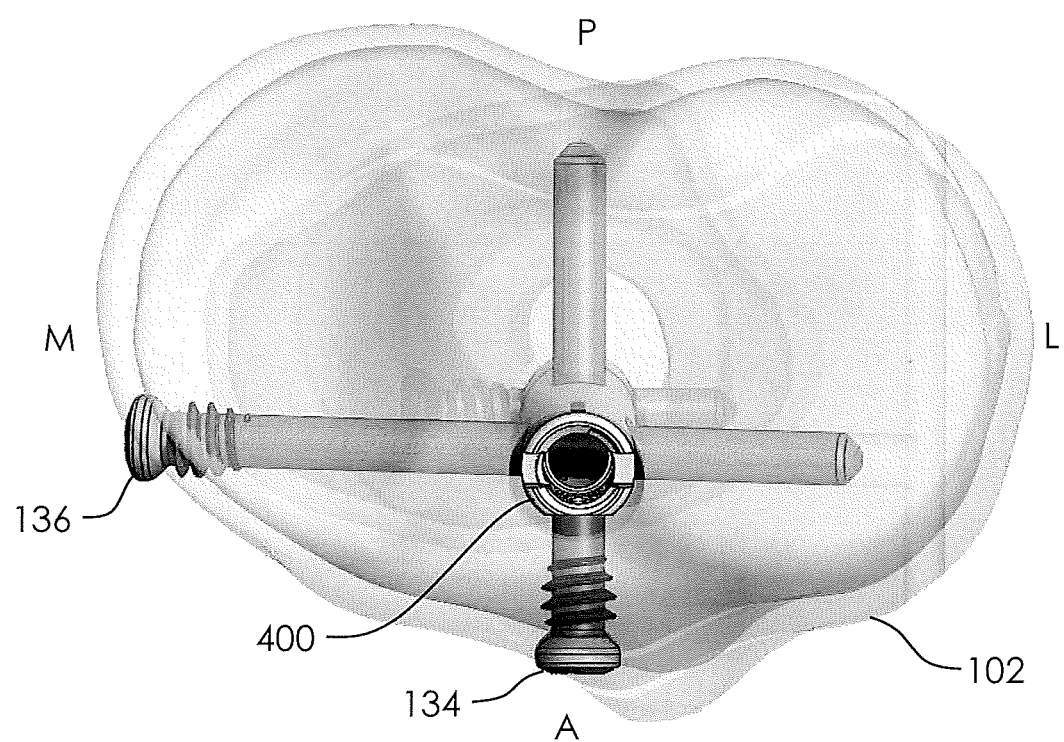
FIG. 17 illustrates a top view of a non-invasively adjustable wedge osteotomy device in place within a tibia.

FIGS. 15-17 show the non-invasively adjustable wedge osteotomy device 400 implanted within a tibia 102 having a medullary canal 130. A hole 132 is drilled along a portion of the length of the medullary canal 130, for example by a series of drills or reamers. An osteotomy 118, which may be either a single cut or a series of cuts (e.g., a wedge), is made in the tibia 102 to separate the tibia 102 into a first portion 119 and a second portion 121. In some cases, a drill hole 452 may be made, and then a blade used to make the cut of the osteotomy 118, up to the point of the drill hole 452. A hinge 450 is thus created at the uncut portion of the tibia 102. Alternatively, the osteotomy 118 may be made entirely through the tibia 102 (such an osteotomy is not shown) and a hinge-like device may be secured to the lateral side of the tibia 102, adjacent the osteotomy. The hinge-like device may comprise or be similar to the Hinge Pediatric Plating System™ sold by Pega Medical of Laval, Quebec, Canada. In this alternative method, the incision and osteotomy could be made from the lateral side instead of the medial side, leaving the medial side without an incision.

Returning to the configurations of FIGS. 15-17, a non-invasively adjustable wedge osteotomy device, such as that shown in FIGS. 10-14, is inserted into the hole 132 and secured to the tibia 102 with bone screws (e.g., two or more bone screws 134, 136, 138, 140, 142). In some embodiments, such as those shown in FIGS. 15-17, the outer housing 430 is secured to the first portion 119 of the tibia 102 with a first bone screw 134 delivered through the first transverse hole 405, and a second bone screw 136 delivered through the slotted transverse hole 407. The inner shaft 432 is secured to the second portion 121 of the tibia 102 with three bone screws 138, 140, 142 delivered through the three transverse holes 464A, 464B, 464C, respectively. As described, the slotted transverse hole 407 may be configured to allow the second bone screw 136 to pivot or rock over an angular range, as will be described further with respect to FIGS. 18-22. As shown in FIGS. 15-17, the first bone screw 134 may be substantially aligned along an Anterior-Posterior axis (i.e., front to back), and the second bone screw 136 may be substantially aligned along the Medial-Lateral axis (i.e., side to side), though in both cases, other degrees of angulation are also contemplated. The non-invasively adjustable wedge osteotomy device 400 is configured to non-invasively distract the first portion 119 of the tibia 102 away from the second portion 121 of the tibia 102, to angularly open the osteotomy 118. With the orientation of the first bone screw 134 and second bone screw 136 shown in FIG. 17, the first bone screw 134 may be free to rotate within the hole 405 (FIG. 16), and the second bone screw 136 may pivot within the slotted transverse hole 407 (FIGS. 15-16).

Figure 20:
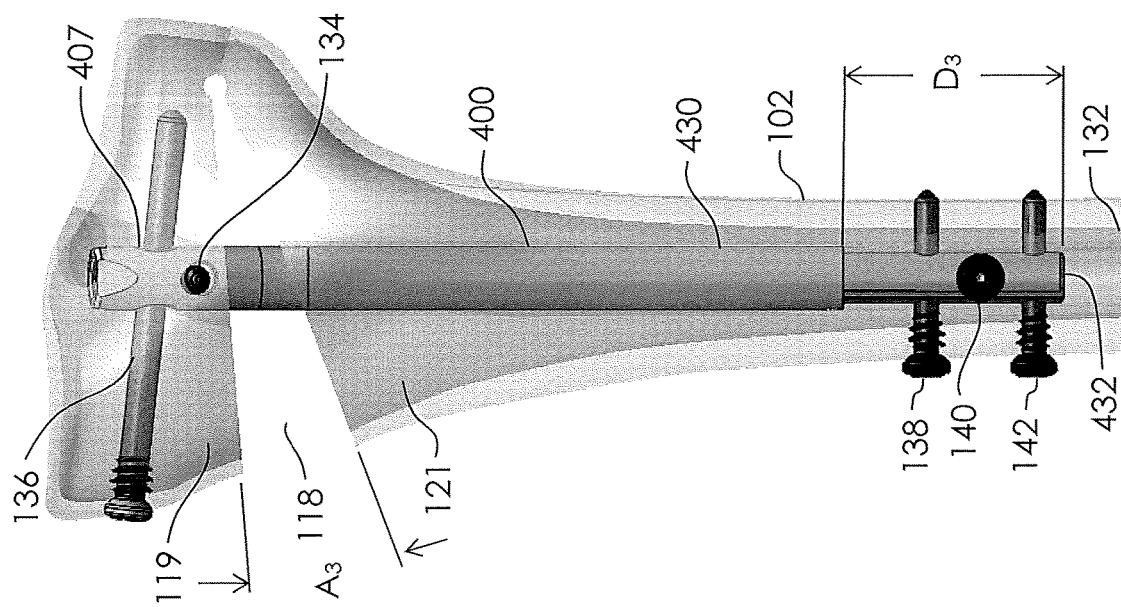
FIG. 20 illustrates a non-invasively adjustable wedge osteotomy device within a tibia in a second adjusted state.
Figure 22:
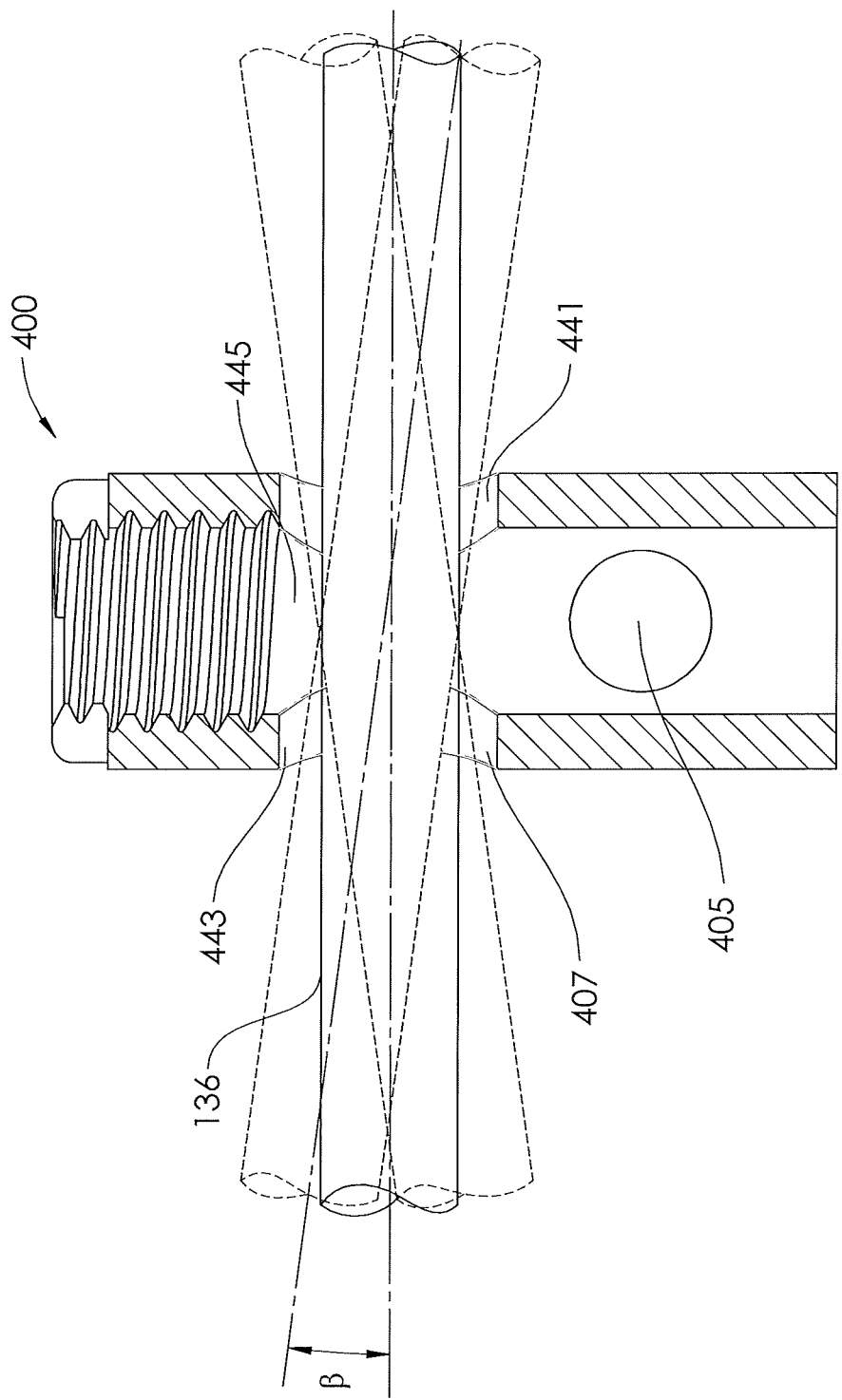
FIG. 22 illustrates a bone screw within a slotted transverse hole of a non-invasively adjustable wedge osteotomy device.

FIG. 22 demonstrates the pivotability of a bone screw in place within a slotted transverse hole (e.g., the second bone screw 136 within the slotted transverse hole 407). The bone screw may pivot through a pivot angle $\beta$ in either direction $(+\beta, -\beta)$. FIGS. 18-20 demonstrate the non-invasively adjustable wedge osteotomy device 400 which is implanted in the tibia 102 being adjusted to increase an angle A of the wedge osteotomy 118. In FIG. 18, the inner shaft 432 extends from the outer housing 430 an initial length $D_1$. The osteotomy 118 is in an initial closed or mostly closed state, and the first bone screw 136 has been secured to the first portion 119 of the tibia 102 so that it is angled at, near, or towards a first extreme of pivot in a first angular direction in relation to the slotted transverse hole 407. More specifically, the head 144 of the first bone screw 136 on the medial side of the first portion 119 is at a lower height in comparison to the distal end 148 on the lateral side of the first portion 119, leaving the first bone screw at an angle $-\beta$ (see FIG. 22). Though the bone screws in FIGS. 18-20 are shown with short proximal male threads 146, other bone screws may be used, including, for example, lag screws, or fully threaded screws. In FIG. 19, a distraction of the non-invasively adjustable wedge osteotomy device 400 has been performed, causing the inner shaft 432 to extend from the outer housing 430 so that it extends a new length $D_2$, which is greater than the initial length $D_1$. In some embodiments non-invasive distraction may be accomplished by placing the magnetic handpiece 1178 of the external adjustment device 1180 on the skin or clothing in the area of the upper tibia 102 and operating the external adjustment device 1180 to rotate the one or more magnets 1186 which in turn cause the radially-poled permanent magnet 368 (FIGS. 6-7) within the non-invasively adjustable wedge osteotomy device 400 to be magnetically rotated. Extension of the inner shaft 432 out of the outer housing 430 causes the first portion 119 to be lifted away from the second portion 121 thereby opening osteotomy 118 to a wedge angle $A_2$. As osteotomy 118 is opened, the first bone screw 136, which is secured to the first portion 119 of the tibia 102, may be rotated with the first portion 119 (the rotation being allowed/facilitated by the slotted transverse hole 407). In FIG. 19, the first bone screw 136 is shown with a substantially horizontal orientation (i.e., $\beta \approx 0°$). In FIG. 20, additional distraction has been performed (e.g., non-invasive distraction) and the inner shaft 432 has been extended further from the outer housing 430 so that it extends a new, increased length $D_3$. A new, increased wedge angle $A_3$ of the osteotomy results from the additional extension of the inner shaft 432, and the first bone screw 136 has pivoted along with the continued rotation of the first portion 119 of the tibia 102 until the first bone screw 136 is angled at, near, or towards a second extreme of pivot in a second angular direction in relation to the slotted transverse hole 407. More specifically, the head 144 of the first bone screw 136 on the medial side of the first portion 119 is at a higher height in comparison to the distal end 148 on the lateral side of the first portion 119, leaving the first bone screw at an angle+β (see FIG. 22).

Non-invasive distraction while a patient is awake, mobile, and or weight-bearing may allow an optimum wedge angle A to be achieved. In some embodiments, an optimum wedge angle is the wedge angle A at which the patient feels no pain. In other embodiments, an optimum wedge angle is the wedge angle A at which the patient feels no contact of tissue at the knee joint, for example at a medial compartment of the knee joint. In some cases, the wedge angle A may be increased until an anatomical benchmark is reached, for example a Fujisawa overcorrection, which is described further below. Distractions may be done at specific time intervals. For example, the total length of a non-invasively adjustable wedge osteotomy device, as disclosed herein, may be increased about 0.5 mm-1.5 mm per day, or about 0.75 mm-1.25, or any other clinically advantageous rate, until the desired wedge angle is reached. Alternatively, the amount by which a non-invasively adjustable wedge osteotomy device, as disclosed herein, is to be lengthened may be calculated prior to each adjustment procedure (e.g., lengthening, distraction, or adjustment), so that a consistent wedge angle increase (i.e., using trigonometric relationships so that the angle can be increased by a consistent $\Delta\beta$) is achieved by each adjustment procedure. In some circumstances, any given day's adjustment may be all at once, within a single procedure. Alternatively, any given day's adjustment may be broken up into two or more smaller adjustments or procedures per day (equivalent to the daily desired total). Breaking up adjustments into smaller procedures may advantageously help to minimize pain or discomfort caused by stretching of soft tissue in the knee joint 104. For some patients or in some circumstances it may be desirable to determine the desired rate of device distraction based on a rate of medial cortex increase (the open portion of the osteotomy 118 at the medial edge of the tibia 102). For example, it may be desirable to distract the device at a rate sufficient to cause the medial cortex to increase by about 1 mm per day: depending on the width of the tibia 102, among other factors, such a 1 mm daily medial cortex increase may require only between about 0.5 mm and 0.65 mm daily device distraction (i.e., daily increase at the midline). In some cases, once the ultimate desired wedge angle is reached, distraction is stopped, and the wedge osteotomy 118 is allowed to consolidate over a period of time (e.g., days, weeks, or months). The amount of time required for consolidation may depend on the angle of wedge osteotomy 118 increase, the rate of wedge osteotomy increase, whether the patient smokes, whether the patient has diabetes, and the patient's activity level, among other biological factors. During the distraction process (e.g., from implantation to substantial healing), it may be desirable for the patient to place a diminished (i.e., less than normal) amount of force (compression) on the leg being treated, for example, through the use of crutches, braces, wheel chairs, walkers, or the like. Additionally, the patient may be instructed to increase the load placed on the leg during the consolidation phase: compression during consolidation has been positively linked to improved osteogenesis and faster and better healing of the bone.

Figure 21:
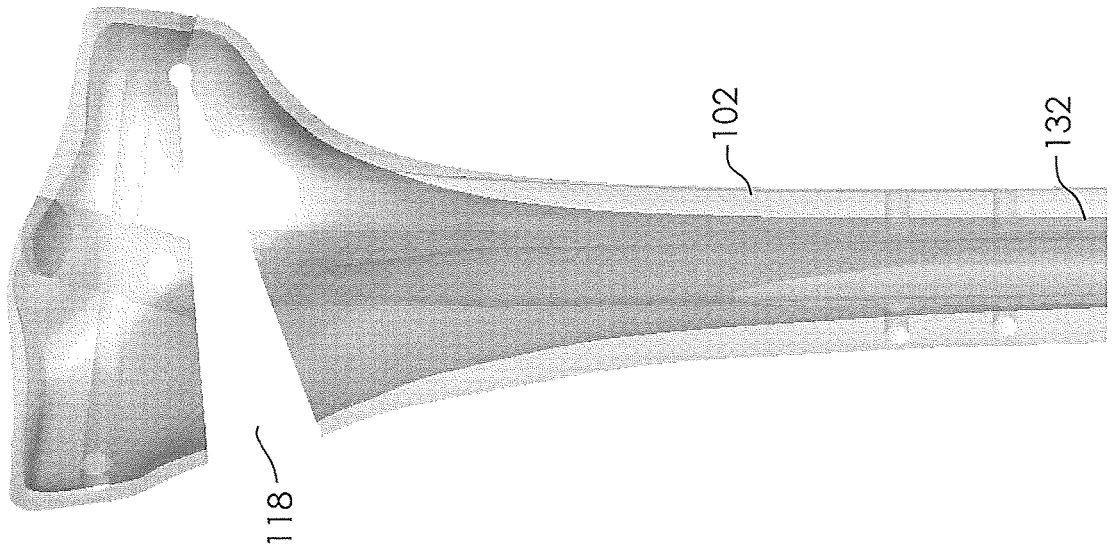
FIG. 21 illustrates a consolidated tibia after removal of a non-invasively adjustable wedge osteotomy device.

In some cases, after the consolidation phase has substantially completed, the devices discloses herein, including the non-invasively adjustable wedge osteotomy device 400 and the bone screws 134, 136, 138, 140, 142 may be removed. A revised tibia 102, after removal of a the non-invasively adjustable wedge osteotomy device, as disclosed herein, is shown in FIG. 21. During the distraction phase and/or the consolidation phase, bone graft may be added to portions of the wedge osteotomy 118 in order to help increase solidification of the tibia 102, for example, between the first portion 119 and the second portion 121.

Figure 30:
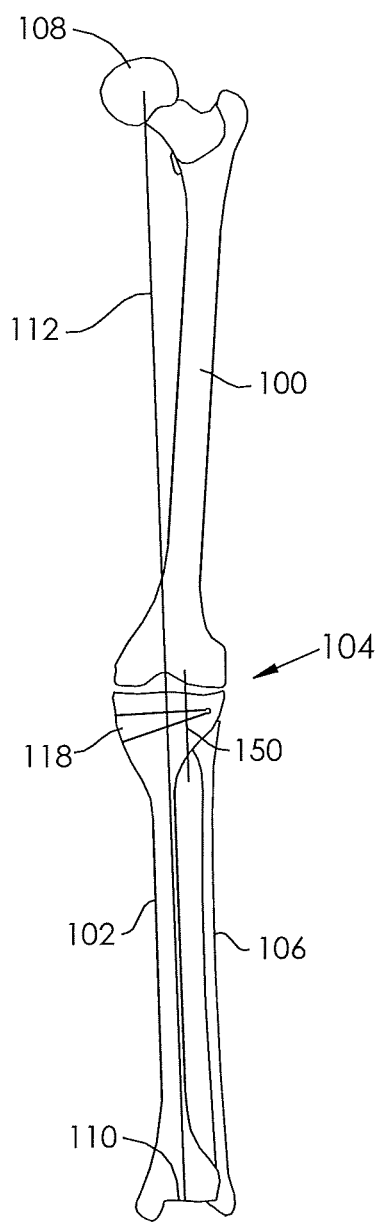
FIG. 30 illustrates a standard correction for the alignment of a knee joint.
Figure 31:
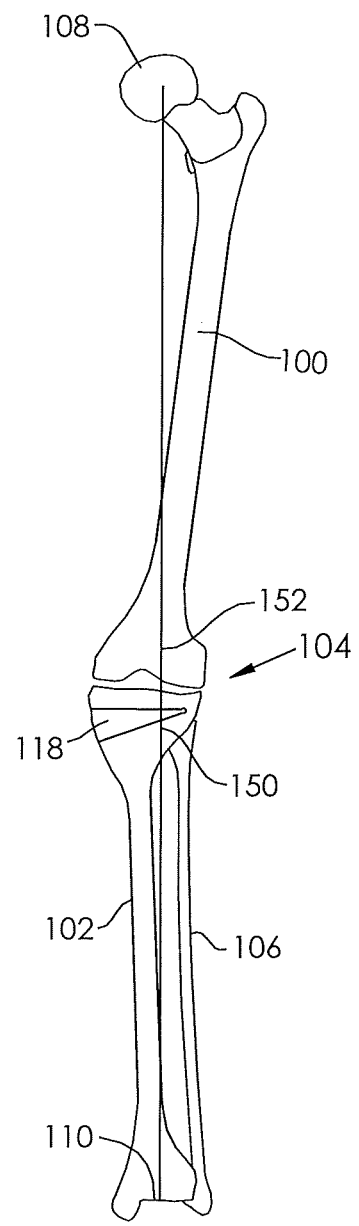
FIG. 31 illustrates a planned overcorrection for the alignment of a knee joint.

FIG. 30 shows the mechanical axis 112 of a tibia 102 that has been adjusted by creating a wedge osteotomy, for example, by using standard methods or the apparatuses and/or methods described herein. The mechanical axis extends from the femur head 108, through the center of the knee joint 104, and to a center point of the ankle joint at the distal tibia 110. Although restoring the mechanical axis 112 through the center of the knee joint 104 has been standard practice in some centers, an alternative method was proposed by Fujisawa (see Fujisawa et al., "The Effect of High Tibial Osteotomy on Osteoarthritis of the Knee: An Arthroscopic Study of 54 Knee Joints", July 1979, Orthopedic Clinics of North America, Volume 10, Number 3, Pages 585-608, the entirety of which is incorporated by reference herein). Fujisawa states that "the ideal correction method is to align the mechanical axis to pass through a point 30 to 40 percent lateral to the midpoint." (Fujisawa et al. at Pages 606-607) An overcorrection axis 150, as taught by Fujisawa, is shown in FIGS. 30-31 and passes through the knee joint 104 at a point that is about 30%-40% lateral of the midpoint in the knee joint 104. As the standard mechanical axis passes through the midpoint in the knee joint 104, the overcorrection axis 150 is about the same percentage lateral to the standard mechanical axis 112. FIG. 31 shows an overcorrection performed by wedge osteotomy of the tibia 102 that reaches approximately the conditions described by Fujisawa. An overcorrected mechanical axis 152 approximates the overcorrection axis 150 through the knee joint 104, extending from the center of the femur head 108 through the knee joint at approximately the overcorrection axis 150, and to the center point of the ankle joint at the distal tibia 110. To achieve overcorrection, the angle of the wedge osteotomy 118 has been increased an additional amount.

Figure 32:
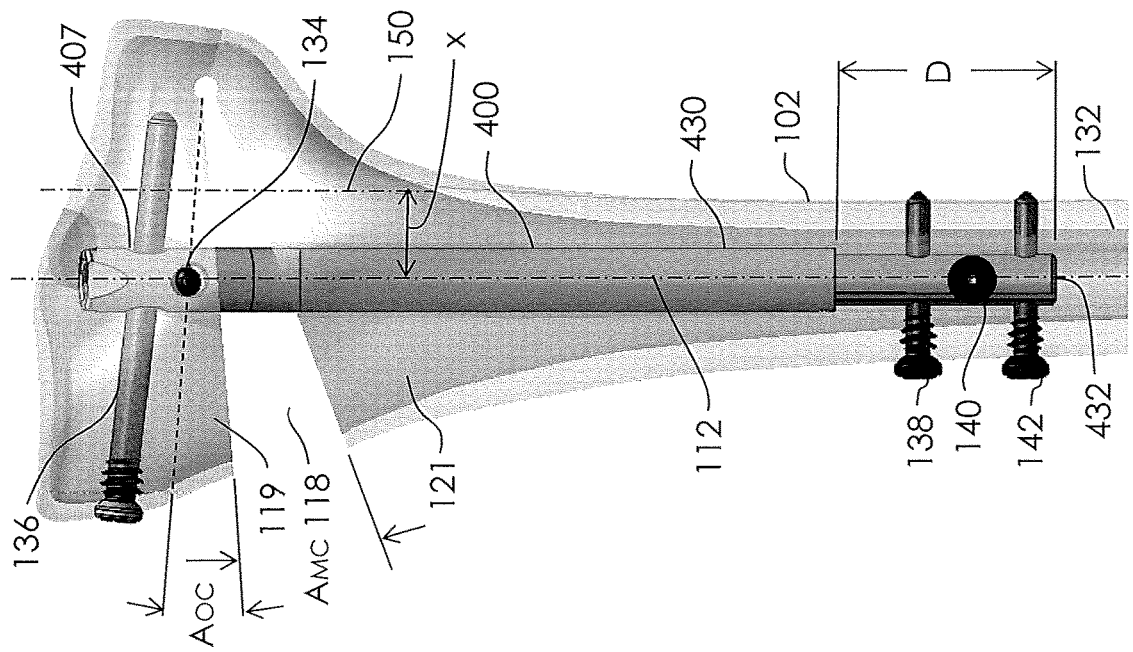
FIG. 32 illustrates a non-invasively adjustable wedge osteotomy device within a tibia in relation to a standard correction axis and a planned overcorrection axis.

FIG. 32 illustrates an embodiment of a non-invasively adjustable wedge osteotomy device, for example the non-invasively adjustable wedge osteotomy device 400, in place within the tibia 102, with the standard mechanical axis 112 and the overcorrection axis 150 indicated. Overcorrection axis 150 is shown a distance x lateral to the standard mechanical axis. In some embodiments, distance x is between about 24%-44%, about 28%-40%, about 30%-38%, and about 32-36% of the total distance from the midline to the lateral extreme. In FIG. 32, the angle of midline correction ("$A_{MC}$") was performed in order to achieve the mechanical axis 112 as shown. The $A_{MC}$ is defined as the amount of angle of correction required to place the mechanical axis through the center of the knee joint 104, may be up to about 12° or less in many patients, and may be achieved by using non-invasively adjustable wedge osteotomy devices as disclosed herein. In some cases, an angle of greater than 12° is required to achieve a proper overcorrection as described above (e.g., it may be desirable in some patients to achieve an angle of up to about 16°, or even more). Thus, an additional angle of overcorrection ("$A_{OC}$"), may be needed in order to create the overcorrected mechanical axis 152 as in FIG. 31. In some cases the $A_{OC}$ may be between about 1°-8°, about 2°-7°, about 3°-6°, and about 4°-5°, or the $A_{OC}$ may be any other angle that is physiologically beneficial for the patient. The total resulting correction angle is therefore equal to the sum of angles $A_{MC}$ and $A_{OC}$.

Another embodiment of a non-invasively adjustable wedge osteotomy device 500, illustrated in FIGS. 23-25, may be configured to allow for an increased amount of angular correction in the tibia 102. The non-invasively adjustable wedge osteotomy device 500 includes an inner shaft 532, which is telescopically distractable from an outer housing 530. In some embodiments, the internal components of the non-invasively adjustable wedge osteotomy device 500 may be similar or identical to those of the other non-invasively adjustable wedge osteotomy devices disclosed herein (for example the non-invasively adjustable wedge osteotomy device 300 of FIGS. 5-6, among others). In some embodiments, a slotted transverse hole 507 extends through the outer housing 530 of the non-invasively adjustable wedge osteotomy device 500. The slotted transverse hole 507 has a generally oblong shape, similar to that described with respect to the embodiments of the non-invasively adjustable wedge osteotomy device shown in FIGS. 10-14. Additionally, the outer housing 530 may have a second slotted hole 586. While the slotted transverse hole 507 may be generally vertically oblong, the second slotted hole 586 may be generally horizontally oblong. The second slotted hole 586 may have a length L and a width W, as shown in FIG. 24. The length L may be configured to be slightly larger than the diameter of a bone screw that is used to secure the non-invasively adjustable wedge osteotomy device 500 to a bone, such that the bone screw is able to pass through the second slotted hole 586. The width W may be chosen such that the bone screw is able to horizontally pivot or angularly displace within the second slotted hole 586. In some embodiments the second slotted hole 586 is configured to be used with a 5 mm bone screw, the length L may be about 5 mm to about 5.2 mm, or about 5.1 mm, and the width W may be about 6 mm to about 9 mm or about 7 mm. In some embodiments, the ratio of width W to length L (i.e., W/L) may be between about 1.08 and about 1.65, or about 1.25 to about 1.54, or about 1.37. The slotted transverse hole 507 and the second slotted hole 586 are located near a first end 568 of the outer housing 530. As shown in FIG. 25, a second end 570 of the outer housing 530 is angled from the first end 568 at a transition point 572. In some embodiments, the angle 578 is between about 2°-18°, about 4°-16°, about 6°-14°, about 8°-12°, and about 10°, or any other angle that is clinically meaningful for any given patient. The second slotted hole 586 may include an anterior opening 588 and a posterior opening 590, which may be oriented in relation to the first end 568 at an angle 576. In some embodiments, the angle 576 is between about 70°-100°, about 75°-95°, about 80°-90°, or about 85°, or any other angle that is clinically meaningful for any given patient. FIG. 23 also illustrates an interface 566 having an internal thread 597, which may be used for releasable detachment of an insertion tool. Similar to what has been described above, the non-invasively adjustable wedge osteotomy device 500 may be inserted by hand or may be attached to an insertion tool (for example a drill guide). In some embodiments, an interface 566 comprising an internal thread 597 is located at or near the first end 568 for reversible engagement with male threads of an insertion tool. Alternatively, such engagement features may be located at or near the inner shaft 532. In other embodiments a tether (e.g., a detachable tether) may be attached to either end of the non-invasively adjustable wedge osteotomy device 500, so that it may be easily removed if placed incorrectly.

Figure 26:
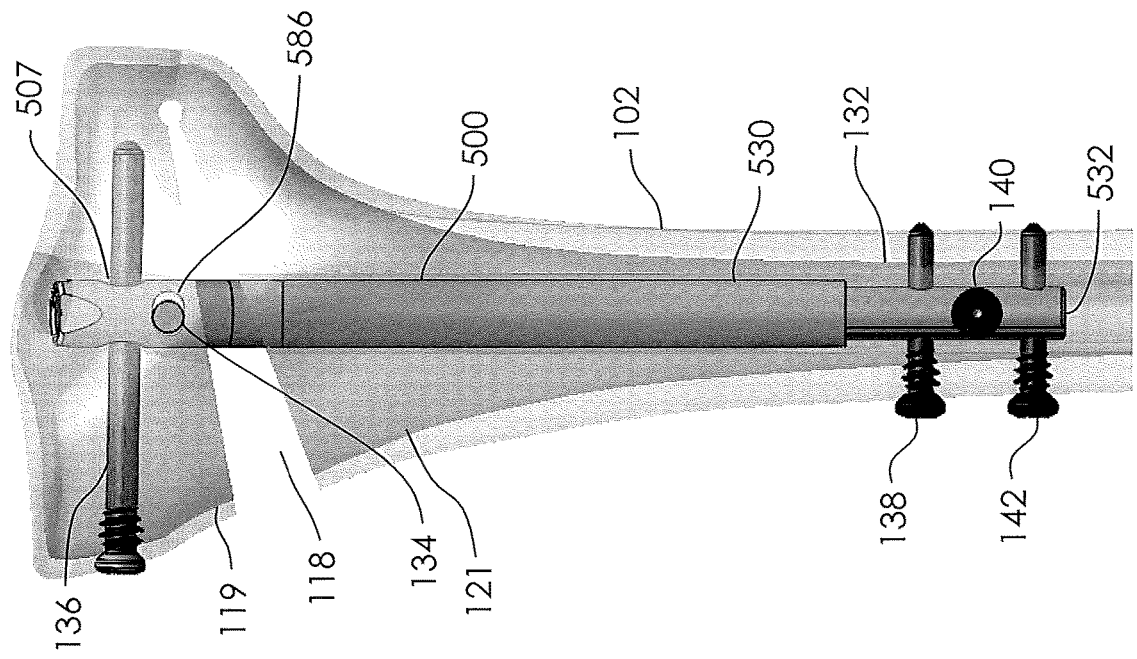
FIG. 26 illustrates the non-invasively adjustable wedge osteotomy device of FIG. 23 within a tibia in a substantially non-adjusted state.
Figure 27:
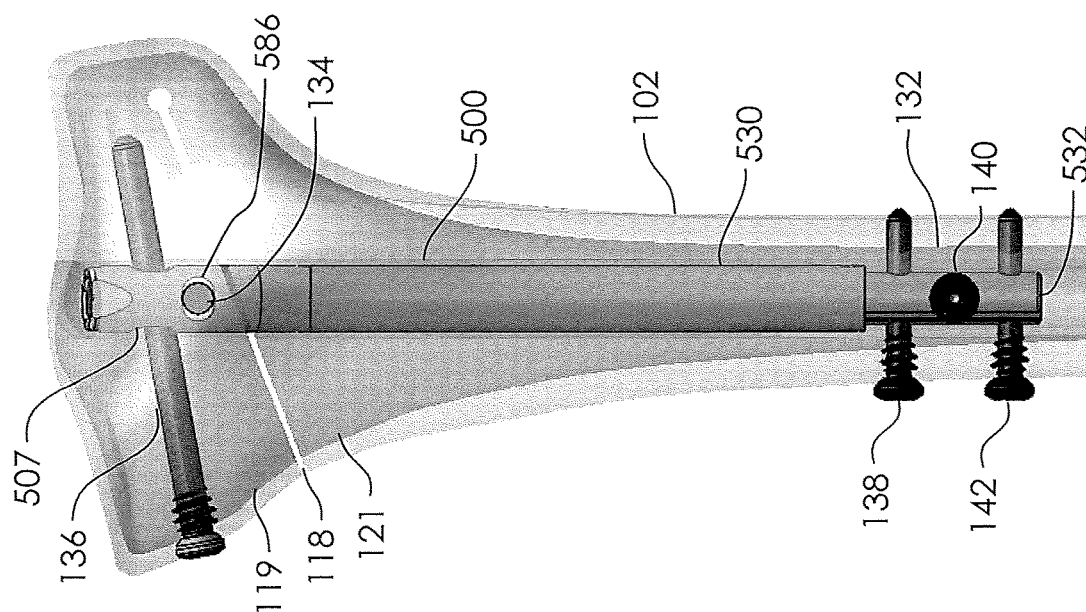

FIGS. 26-29 illustrate how the second slotted hole 586 of the non-invasively adjustable wedge osteotomy device 500 works in conjunction with the slotted transverse hole 507 to advantageously facilitate the possibility of an increased amount of angular correction between a first portion 119 and second portion 121 of the tibia 102. First bone screw 134 is illustrated without a head merely so the shaft of the first bone screw 134 is visible within the second slotted hole 586. In FIG. 26, the osteotomy 118 is substantially closed and the inner shaft 532 has not been significantly distracted from the outer housing 530. The first bone screw 134 may (at least initially) preferably be centrally oriented with respect to the width W of the second slotted hole 586. In FIG. 27, the inner shaft 532 has been distracted further out of the outer housing 530. As the outer housing 530 moves, it pushes up on the first bone screw 134 and the second bone screw 136, which in turn push upward on the first portion of the tibia 102, causing the first portion of the tibia 119 to pivot about the hinge. As the first portion of the tibia pivots, the second bone screw 136 pivots within the slotted transverse hole 507, as described with respect to other embodiments disclosed herein, such as the non-invasively adjustable wedge osteotomy device 400. While the second bone screw 136 pivots, the first bone screw 134 may slide medially (i.e., towards the left side of FIG. 27). In FIG. 28, the inner shaft 532 has been distracted still further out of the outer housing 530. As the second bone screw 136 pivots even further within the slotted transverse hole 507, the first bone screw 134 may be forced back towards a central location with respect to the width W of the second slotted hole 586. In FIG. 29, the inner shaft 532 is distracted still further out of the outer housing 530, and, as the second bone screw 136 pivots still further within the slotted transverse hole 507, the first bone screw 134 may slide laterally (i.e., towards the right side of FIG. 27). The elongated orientation of the second slotted hole 586 along the width W, may advantageously add additional freedom to the movement of the non-invasively adjustable wedge osteotomy device 500 as it distracts the first portion 119 from the second portion 121 of the tibia 102, and allow for an increased amount of angulation, for example, a total of between about 10°-22°, about 12°-20°, about 14°-18°, or about 16°, or any other degree of angulation that is clinically meaningful for any given patient. Devices (e.g., other non-invasively or invasively adjustable wedge osteotomy devices, including those disclosed herein) that do not have both the slotted transverse hole 507 and second slotted hole 586, may be able to achieve about 16° of angulation. However, for such devices to do so may cause axial lengthening between the first portion 119 and the second portion 121 of the tibia 102, as opposed to merely changing the angle between the first portion 119 and the second portion 121. Axial lengthening between the first portion 119 and the second portion 121 of the tibia may cause unneeded and deleterious stresses on and/or even fracture of the hinge 450 formed by the connection between the first portion 119 and the second portion 121 of the tibia 102 (shown in FIG. 15). Were the first portion 119 to fracture from the second portion 121 and away from the rest of the tibia 102, the first portion 119 could be axially or non-angularly distracted away from the second portion 121, and would not correct the angle of the knee joint 104. Therefore, incorporation of both the slotted transverse hole 507 and second slotted hole 586 into the non-invasively adjustable wedge osteotomy device 500 may allow a full 16° of angulation (or more) with little to no axial elongation, which can be advantageously achieved without significant damage to the hinge 450. In some cases, angulation of up to 25° may be possible while still maintaining the same anterior to posterior slope on the top surface of the tibia 102.

In some embodiments, an alternative to the slotted transverse hole 407, 507 may be used. FIGS. 33-34 illustrate an hourglass shaped hole for enabling pivoting of a bone screw. Wall 602 (for example, of non-invasively adjustable wedge osteotomy device 600) may have a tapered or hourglass-shaped hole 606 passing through the wall 602. The tapered or hourglass-shaped hole 606 may have a circular cross-section that varies in diameter along its length. As the wedge osteotomy device distracts/retracts, as disclosed herein, the second bone screw 136 is allowed to pivot, for example, from the position in FIG. 33 to the position in FIG. 34. The degree of pivot is directly dependent on the variance in diameter: the larger the outer diameter, the more pivot is allowed. It is contemplated that embodiments of the tapered or hourglass-shaped hole 606 may permit pivot angles (i.e., the degree of maximum pivot to maximum pivot, such as the angular difference between the second bone screw 136 shown in FIG. 33 to the second bone screw 136 shown in FIG. 34) of between about 5°-40°, about 10°-35°, about 15°-30°, and about 20°-25°, or any other angle that is clinically meaningful for any given patient.

In some embodiments, other alternatives to the second slotted hole 586, as illustrated in FIGS. 35-37, may be used. FIGS. 35-37 illustrate an eccentric bearing type hole for enabling pivoting of a bone screw. For example, hole 626 may be incorporated into the wall of a non-invasively adjustable wedge osteotomy device as is disclosed herein, such as non-invasively adjustable wedge osteotomy device 620. In some embodiments, the hole 626 is configured to extend in a generally anterior to posterior/posterior to anterior orientation when the non-invasively adjustable wedge osteotomy device 620 is implanted in the tibia 102. In other embodiments, the hole 626 is configured to extend in a generally medial to lateral/lateral to medial orientation when the non-invasively adjustable wedge osteotomy device 620 is implanted in the tibia 102. In yet other embodiments, the hole 626 extends through the non-invasively adjustable wedge osteotomy device 620 at an angle between medial to lateral, and anterior to posterior. In some embodiments, the hole 626 may extend through the non-invasively adjustable wedge osteotomy device 620 at an angle substantially perpendicular to the longitudinal axis of the non-invasively adjustable wedge osteotomy device 620. In other embodiments, the hole 626 may extend through the non-invasively adjustable wedge osteotomy device 620 at an angle not perpendicular to the longitudinal axis of the non-invasively adjustable wedge osteotomy device 620, for example about 1°-30° off perpendicular, about 2°-25° off perpendicular, about 3°-20° off perpendicular, about 4°-15° off perpendicular, or about 5°-10° off perpendicular, or any other angle off perpendicular that is clinically meaningful to any given patient. An eccentric bearing 622 may be rotationally held within the hole 626. The eccentric bearing 622 may be made from a lubricious material (e.g., PEEK, UHMWPE, etc.) so as to advantageously decrease friction in the system. The eccentric bearing 622 has an off-center hole 628 through which an object may be placed (e.g., the first bone screw 134). When distracting a non-invasively adjustable wedge osteotomy device 620 incorporating an eccentric bearing 622 as shown in FIGS. 35-37, the off-center hole 628 (and thus any object extending through the off-center hole 628, such as the first bone screw 134) rotates in relation to the hole 626, for example, in a first rotational direction 624. FIG. 35 shows a location of approximately seven o'clock; FIG. 36 shows a location of approximately ten o'clock; and FIG. 37 shows a location of approximately two o'clock. The eccentric bearing 622 may be fixedly held within the hole 626 of the non-invasively adjustable wedge osteotomy device 620, for example with snaps, detents, welds, glues, epoxies, or any other means of fixation appropriate for the application. Alternatively, the eccentric bearing 622 may be inserted into the hole 626 by a user. The motion of the first bone screw 134 within the eccentric bearing 622 may have characteristics similar to motion of the first bone screw 134 within the second slotted hole 586 (discussed with respect to FIGS. 26-29), though the eccentric bearing 622 may allow some additional movement of an object extending through the off-center hole with respect to the non-invasively adjustable wedge osteotomy device 620, for example vertical (i.e., up and down) movement of an object extending through the off-center hole 628 in addition to the lateral (i.e., left and right) movement of an object extending through the off-center hole 628.

Figure 38:
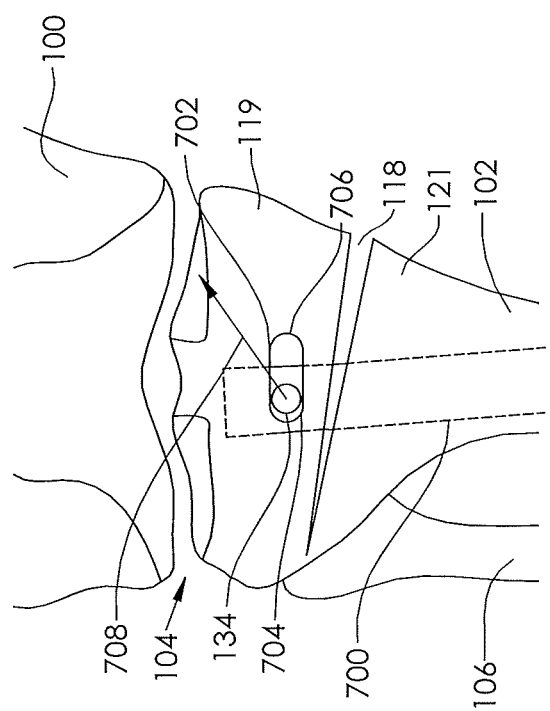

In FIG. 38, an elongated hole 702 has been cut or drilled into the upper portion 119 of the tibia 102 in a substantially horizontal fashion. The elongated hole 702 has a first end 704 (shown here laterally) and a second end 706 (shown here medially). A non-invasively adjustable wedge osteotomy device 700, as shown in FIG. 40, may be placed within a drilled or reamed medullary canal within the tibia 102, and a first bone screw 734 inserted through an anchor hole 716 in the non-invasively adjustable wedge osteotomy device 700. In some embodiments, the anchor hole 716 has an internal threaded portion 722 configured to engage a male thread 710 of the first bone screw. The first bone screw 734 has a head 718 and a distal end 720. The elongated hole 702 (shown in FIGS. 38-40) is drilled through the first cortex 712 and the second cortex 714. The distal end 720 of the first bone screw may then be inserted through the elongated hole 702. In some embodiments, including the embodiment shown in FIG. 40, the male thread 710 engages with the first cortex 712 thereby cutting partial threads in the bone of the first cortex 712 and allowing the male thread 710 to pass through the first cortex 712. Once the male thread 710 has passed through the first cortex 712, it is may be threaded into the internal threaded portion 722 of the anchor hole 712, thereby fixing/locking/securing the bone screw 734 to the to the non-invasively adjustable wedge osteotomy device 700. Because the bone screw 734 is only threaded in the middle (i.e., has a smooth neck, and smooth distal end), it may slide or displace along the elongated hole 702 in the upper portion 119 of the tibia 102 from the first end 704 to the second end 706, all while the middle threaded portion remains secured to the non-invasively adjustable wedge osteotomy device 700.

Figure 39:
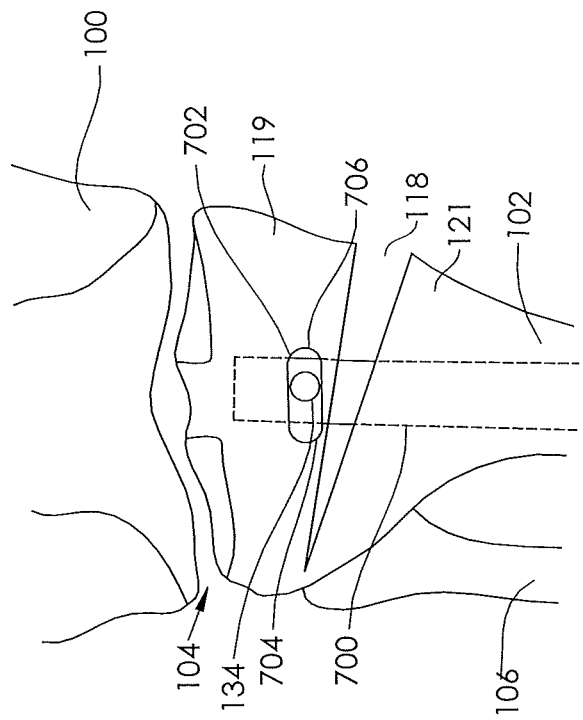
FIGS. 38-39 illustrate a knee joint with a non-invasively adjustable wedge osteotomy device implanted in a tibia in various states of distraction.

As the non-invasively adjustable wedge osteotomy device 700 is distracted, the first bone screw 134, 734 is able to follow a path 708 (shown in FIG. 38) while the angle of the osteotomy 118 increases and as the first bone screw 134, 734 moves away from the first end 704 of the elongated hole 702 and towards the second end 706 of the elongated hole 702, as shown in FIGS. 38 and 39. In some embodiments, the first bone screw 134 may be replaced by a pin that inserts through an anchor hole in the non-invasively adjustable wedge osteotomy device 700. Such a pin may be anchored using a close fit, friction fit, snap fit, spring fit, or the like.

FIGS. 41-42 illustrate an embodiment of a non-invasively adjustable wedge osteotomy device 740 which has been implanted and secured to an upper portion 119 of the tibia 102. Among many other elements, that may be interchangeable with this disclosed elsewhere in this application, the non-invasively adjustable wedge osteotomy device 740 includes a curved anterior-posterior pin 744 and a bone screw 742. The non-invasively adjustable wedge osteotomy device 740 may be configured, as described herein with respect to other embodiments, to allow the bone screw 742 to pivot, displace, slide, or otherwise move during distraction or retraction of the non-invasively adjustable wedge osteotomy device 740. In some embodiments, the curved anterior-posterior pin 744 has a curved central portion 750 that can be inserted through a hole (such as an anchor hole) of the non-invasively adjustable wedge osteotomy device 740, a first straight end 746 and a second straight end 748.

To insert the curved anterior-posterior pin 744, a hole may be drilled in each of the cortices (anterior to posterior/posterior to anterior) of the upper portion 119 of the tibia 102. The curved anterior-posterior pin 744 may be inserted into the hole in the first side of the first portion 119, through the non-invasively adjustable wedge osteotomy device 740, and out of the hole in the second side of the first portion 119. Thereby, the curved anterior-posterior pin 744 may rotationally engage the first portion 119 and the non-invasively adjustable wedge osteotomy device 740 by using the first straight end 746 and the second straight end 748. When the non-invasively adjustable wedge osteotomy device 740 is distracted, the curved anterior-posterior pin 744 may advantageously rotate within the holes (about the first straight end 746 and the second straight end 748), thereby allowing the anchor hole of the non-invasively adjustable wedge osteotomy device 740 to move in a lateral or medial direction and facilitate displacement in multiple axes simultaneously, as described with respect to other embodiments herein.

Figure 44:
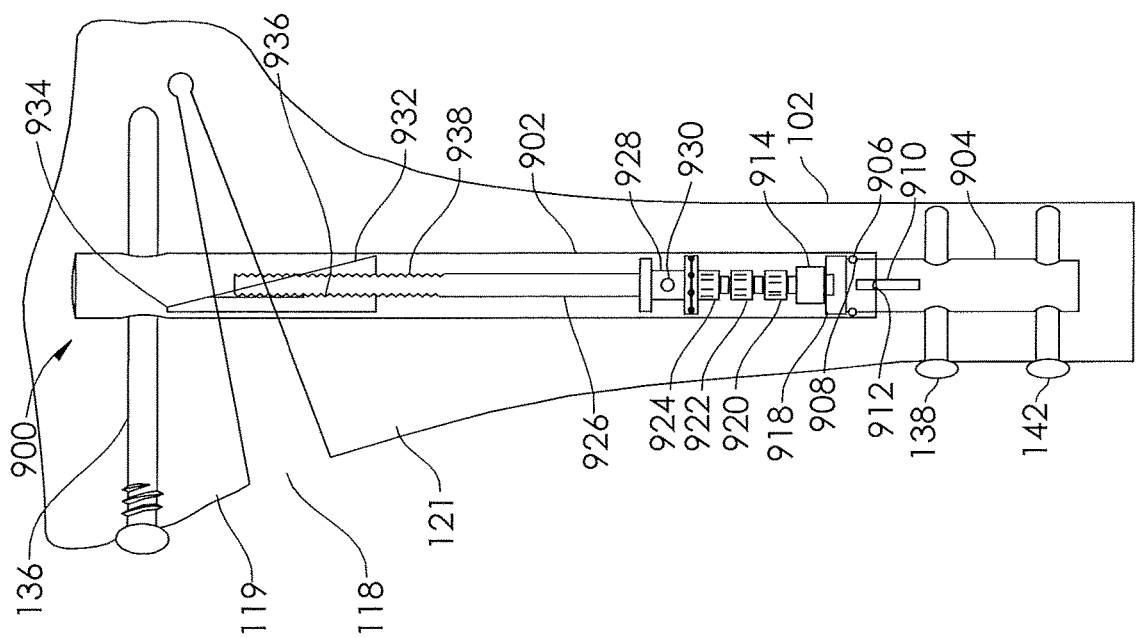
FIGS. 43-44 illustrate a front view of a tibia implanted with another embodiment of a non-invasively adjustable wedge osteotomy device in various states of distraction.
Figure 43:
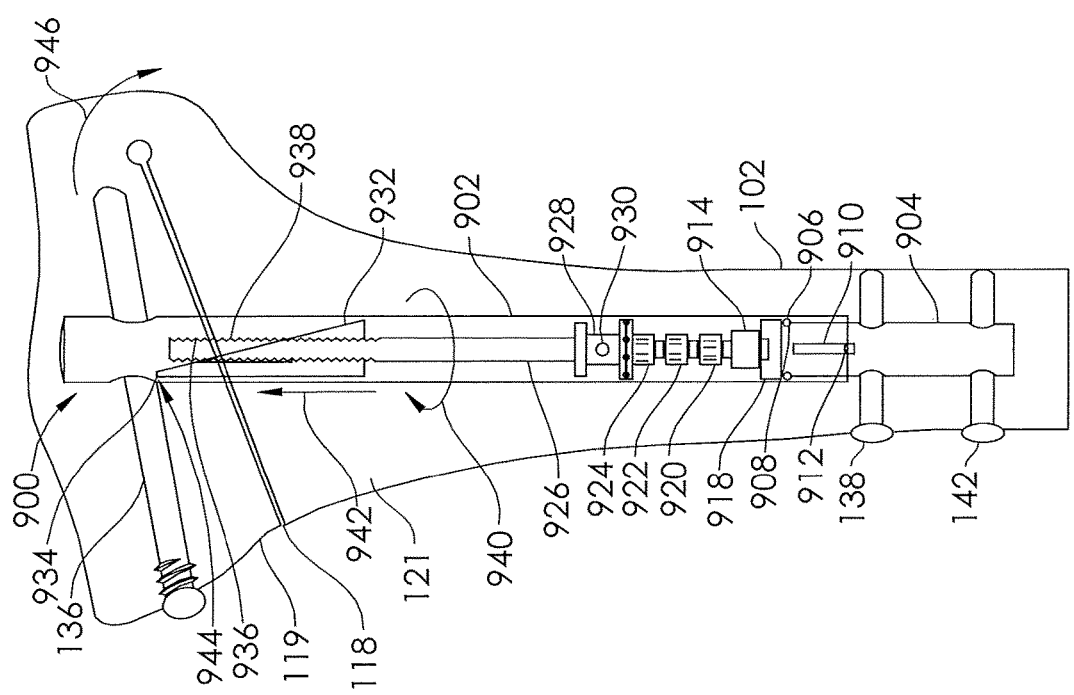

FIGS. 43-44 illustrate an embodiment of a non-invasively adjustable wedge osteotomy device 900 implanted within a tibia 102. The non-invasively adjustable wedge osteotomy device 900 comprises an outer housing 902 and an inner shaft 904, telescopically located within the outer housing 902. FIGS. 43-44 illustrate two distal bone screws 138, 142. But, it should be understood that any number of bone screws may be used. In the same way, FIGS. 43-44 illustrate only a single proximal bone screw 136. Again, it should be understood that this is for illustration purposes only and that more than one bone screw (e.g., 2 bone screws) may be used to anchor the non-invasively adjustable wedge osteotomy device 900 to the first portion 119 of the tibia 102. A second proximal bone screw (similar to the bone screw 134 of FIGS. 15-20) may be incorporated and may provide the advantageous benefit of rotationally stabilizing the upper portion 119 and lower portion 121 of the tibia 102 in relation to the longitudinal axis of the tibia 102.

In some embodiments, the rotational orientation between the outer housing 902 and inner shaft 904 is maintained by a longitudinal groove 910 on the outer surface of the inner shaft 904 and a radial projection 912 extending from the inner surface of the outer housing 902 and configured to slide within the longitudinal groove 910. During actuation, rotation of screw 136 may pull on the outer housing 902 at larger angles; consequently, the outer housing 902 and inner shaft 904 may advantageously be able to longitudinally translate in relation to each other. The inner contents of the non-invasively adjustable wedge osteotomy device may advantageously be protected from the harsh environment within the body. For example, an o-ring seal 906 may be contained within a circumferential groove 908 in the inner portion of the outer housing 902 to provide a dynamic seal between the outer housing 902 and the inner shaft 904.

In some embodiments, a magnet 914 is rotationally carried by the end of the inner shaft 904 via a radial bearing 918. The magnet 914 may be carried within a rotatable magnet housing (not shown). Gear stages 920, 922, 924 couple the magnet 914 to a lead screw 926. The lead screw 926 is coupled non-rigidly to the output of the final gear stage (i.e., gear stage 924) (e.g., by a coupler 928), and may be held in place by a pin 930. The magnet 914 may be rotated by an external moving magnetic field, thereby causing rotation of the lead screw 926. Step-down gear ratios may be used so that several rotations of the magnet 914 are necessary to cause one rotation of the lead screw 926. Additional description and examples of gears stages, such as planetary gear stages, that may be used are included above. In some embodiments, gear stages are not included, leaving a 1:1 ratio (i.e., one rotation of the magnet 914 causes one rotation of the lead screw 926. The rotation of the lead screw 926 causes longitudinal movement of a nut 932, which may have a distal fulcrum 934. An inner thread 936 of the nut 932 threadingly engages an outer thread 938 of the lead screw 926. Rotation of the lead screw 926 in a first rotational direction 940 causes movement of the nut 932 in a first longitudinal direction 942, forcing the distal fulcrum 934 against the bone screw 136 at contact location 944, causing the bone screw 136 and the upper portion 119 of the tibia 102 to generally follow a curved path 946, generally around the contact location 944. In some embodiments, some sliding between the bone screw 136 and the distal fulcrum 934 may occur (that is to say that the distal fulcrum 934 is not a pure fulcrum, which is fixed at a single point with no sliding). The wedge osteotomy 118 is thus caused to open, as shown in FIG. 44. In some embodiments, adjustment of the non-invasively adjustable wedge osteotomy device 900 does not directly cause longitudinal movement of the outer housing 902 with respect to the inner shaft 904 (as has been disclosed with certain other embodiment). Instead, the outer housing 902 and inner shaft 904 may passively move longitudinally with respect to each other, to accommodate length change that may occur as a result of the pivoting of the bone screw 136 and the upper portion 119 of the tibia 102 during the adjustment (for example from the condition in FIG. 43 to the condition in FIG. 44).

FIGS. 45-46 illustrate an embodiment of a non-invasively adjustable wedge osteotomy device 950 implanted within a tibia 102. The non-invasively adjustable wedge osteotomy device 950 includes an outer housing 952 and an inner shaft 954, which is telescopically located within the outer housing 952. FIGS. 45-46 illustrate two distal bone screws 138, 142. But it should be understood that any number of bone screws may be used. A first bone screw 134 is used to secure a pivoting member 956 to the upper portion 119 of the tibia 102. The first bone screw 134 passes through an anchor hole 958. In some embodiments, the anchor hole 958 is configured to allow rotation between the first bone screw 134 and the anchor hole 958 of the pivoting member 956. An angled anchor hole 960 through the pivoting member 956 allows the passage of a second bone screw 136. The angled anchor hole 960 may have a diameter only just larger than the diameter of the bone screw 136. Therefore, when the bone screw 136 is inserted through the angled anchor hole 960, it is held substantially fixed with respect to the pivoting member 956 (i.e., the angled anchor hole 960 does not allow the second bone screw 136 to pivot or rock substantially in relation to the pivoting member 956). The pivoting member 956 may be coupled to the outer housing 952 by a pivot joint 962. The internal components of the non-invasively adjustable wedge osteotomy device 950 may be similar to those described herein with respect to other embodiments, including those shown in FIGS. 5-7.

FIG. 45 shows the non-invasively adjustable wedge osteotomy device 950 in a substantially undistracted condition whereas FIG. 46 shows the non-invasively adjustable wedge osteotomy device 950 in a distracted condition. As the inner shaft 954 is distracted from the outer housing 952, the pivoting member 956, the upper portion 119 of the tibia 102 and the second bone screw 136 pivot—the second bone screw and the pivoting member 956 pivot about the pivot joint 962 in relation to the outer housing 952 and the lower portion 121 of the tibia 102, thus causing the wedge osteotomy 118 to angularly open and the upper portion 119 of the tibia 102 to pivot about the joint/hinge. In some embodiments, the pivoting member 956 may be pivotably coupled to the inner shaft 954, instead of the outer housing 952. In some embodiments, the pivotable joint 962 may be replaced by a ball joint, which allows additional degrees of freedom between the pivoting member 956 and the outer housing 952.

Throughout the embodiments presented, a radially-poled permanent magnet (e.g. 368 of FIG. 6) is used as a noninvasively-actuatable driving element to generate movement in a non-invasively adjustable wedge osteotomy device. FIGS. 47-50 schematically show four alternate embodiments, in which other types of energy transfer are used in place of permanent magnets.

Figure 47:
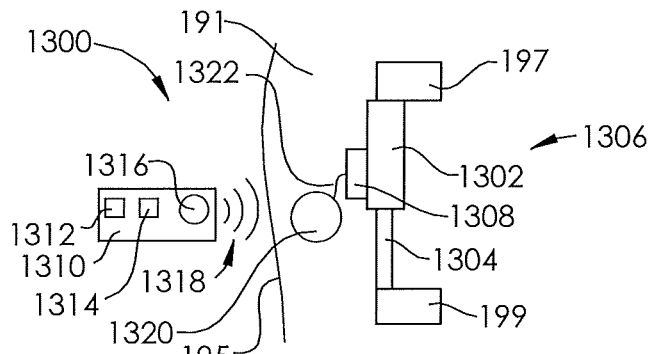
FIGS. 47-50 schematically illustrate various embodiments of a driving element of a non-invasively adjustable wedge osteotomy device.

FIG. 47 illustrates an embodiment of a non-invasively adjustable wedge osteotomy system 1300 including an implant 1306 having a first implant portion 1302 and a second implant portion 1304, the second implant portion 1304 non-invasively displaceable with relation to the first implant portion 1302. The first implant portion 1302 is secured to a first portion of the body 197 and the second implant portion 1304 is secured to a second portion of the body 199 within a patient 191. A motor 1308 is operable to cause the first implant portion 1302 and the second implant portion 1304 to displace relative to one another. In some embodiments, an external adjustment device 1310 has a control panel 1312 for input by an operator, a display 1314, and a transmitter 1316. The transmitter 1316 sends a control signal 1318 through the skin 195 of the patient 191 to an implanted receiver 1320. Implanted receiver 1320 may communicate with the motor 1308 via a conductor 1322. The motor 1308 may be powered by an implantable power source (e.g., a battery), or may be powered or charged by inductive coupling.

Figure 48:
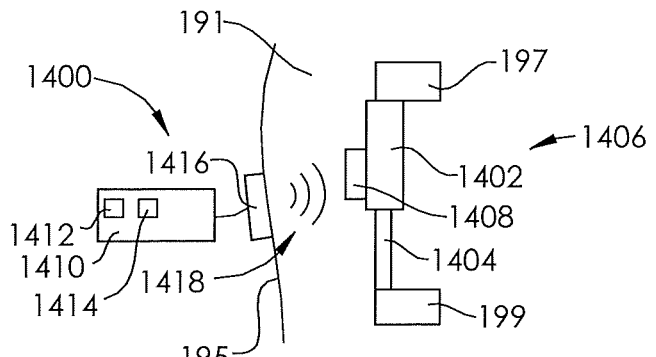

FIG. 48 illustrates an embodiment of a non-invasively adjustable wedge osteotomy system 1400 including an implant 1406 having a first implant portion 1402 and a second implant portion 1404, the second implant portion 1404 non-invasively displaceable with relation to the first implant portion 1402. The first implant portion 1402 is secured to a first portion of the body 197 and the second implant portion 1404 is secured to a second portion of the body 199 within a patient 191. An ultrasonic motor 1408 is operable to cause the first implant portion 1402 and the second implant portion 1404 to displace relative to one another. In some embodiments, an external adjustment device 1410 has a control panel 1412 for input by an operator, a display 1414, and an ultrasonic transducer 1416 that is coupled to the skin 195 of the patient 191. The ultrasonic transducer 1416 produces ultrasonic waves 1418 which pass through the skin 195 of the patient 191 and operate the ultrasonic motor 1408.

Figure 49:
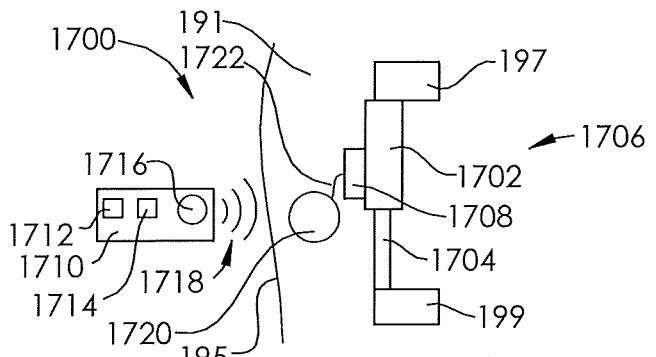

FIG. 49 illustrates an embodiment of a non-invasively adjustable wedge osteotomy system 1700 comprising an implant 1706 having a first implant portion 1702 and a second implant portion 1704, the second implant portion 1704 non-invasively displaceable with relation to the first implant portion 1702. The first implant portion 1702 is secured to a first portion of the body 197 and the second implant portion 1704 is secured to a second portion of the body 199 within a patient 191. A shape memory actuator 1708 is operable to cause the first implant portion 1702 and the second implant portion 1704 to displace relative to one another. In some embodiments, an external adjustment device 1710 has a control panel 1712 for input by an operator, a display, 1714 and a transmitter 1716. The transmitter 1716 sends a control signal 1718 through the skin 195 of the patient 191 to an implanted receiver 1720. Implanted receiver 1720 may communicate with the shape memory actuator 1708 via a conductor 1722. The shape memory actuator 1708 may be powered by an implantable power source (e.g., a battery), or may be powered or charged by inductive coupling.

Figure 50:
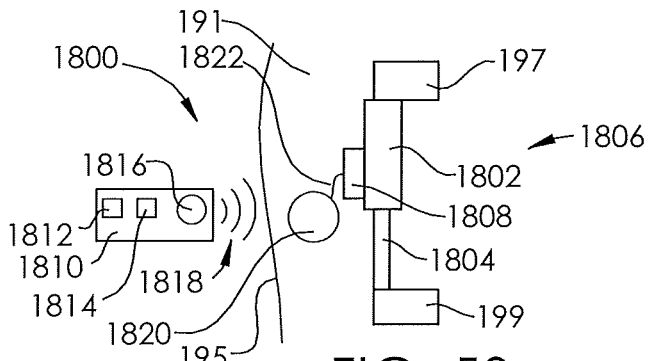

FIG. 50 illustrates an embodiment of a non-invasively adjustable wedge osteotomy system 1800 including an implant 1806 having a first implant portion 1802 and a second implant portion 1804, the second implant portion 1804 non-invasively displaceable with relation to the first implant portion 1802. The first implant portion 1802 is secured to a first portion of the body 197 and the second implant portion 1804 is secured to a second portion of the body 199 within a patient 191. A hydraulic pump 1808 is operable to cause the first implant portion 1802 and the second implant portion 1804 to displace relative to one another. In some embodiments, an external adjustment device 1810 has a control panel 1812 for input by an operator, a display, 1814 and a transmitter 1816. The transmitter 1816 sends a control signal 1818 through the skin 195 of the patient 191 to an implanted receiver 1820. Implanted receiver 1820 communicates with the hydraulic pump 1808 via a conductor 1822. The hydraulic pump 1808 may be powered by an implantable power source (e.g., a battery), or may be powered or charged by inductive coupling. The hydraulic pump 1808 may alternatively be replaced by a pneumatic pump.

In some embodiments of the wedge osteotomy devices disclosed herein, the slotted holes may be located on the inner shaft instead of or in addition to the outer housing. The orientation of the implant within the tibia may be opposite of that illustrated in any of the figures. Additionally, any of the embodiments of the non-invasively adjustable wedge osteotomy device may be used for gradual distraction (Ilizarov osteogenesis) or for acute correction of an incorrect angle. And, in some embodiments, alternative, remote adjustment described above may be replaced by manual control of any implanted part, for example manual pressure by the patient or caregiver on a button placed under the skin.

Of course, the foregoing description is of certain features, aspects and advantages of the present invention, to which various changes and modifications can be made without departing from the spirit and scope of the present invention. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of the specific features and aspects between and among the different embodiments may be made and still fall within the scope of the invention. Accordingly, it should be understood that various features and aspects of the disclosed embodiments can be combined with or substituted for one another in order to form varying modes of the discussed devices, systems and methods (e.g., by excluding features or steps from certain embodiments, or adding features or steps from one embodiment of a system or method to another embodiment of a system or method).

The invention claimed is:

1. A non-invasively adjustable implant, comprising:
    an outer housing associated with a first anchor hole configured to receive a first anchor therethrough, the first anchor being configured to couple the adjustable implant to a first portion of bone,
    wherein the first anchor hole is slotted with a raised portion that is integrally formed on a surface located therein, the raised portion being configured to allow the first anchor to pivot in at least a first angular direction;
    an inner shaft telescopically disposed in the outer housing, the inner shaft configured to couple to a second portion of bone that is separated from the first portion of bone, such that non-invasive elongation of the adjustable implant causes the inner shaft to extend from the outer housing and to move the first portion of bone relative to the second portion of bone; and
    a driving element disposed within the outer housing and configured to be remotely operable to telescopically displace the inner shaft in relation to the outer housing.

2. The implant of claim 1, wherein the first anchor hole is configured to allow the first anchor to pivot in a second angular direction, opposite the first angular direction.

3. The implant of claim 1, comprising a second anchor hole configured to receive a second anchor therethrough, the second anchor hole being configured to allow the second anchor to translate in a first translation direction.

4. The implant of claim 3, wherein the second anchor hole is configured to allow the second anchor to translate in a second translation direction, opposite the first translation direction.

5. The implant of claim 3, wherein the first anchor hole extends substantially along a first plane approximating a radial section of the adjustable implant and the second anchor hole extends substantially along a second plane approximating a radial section of the adjustable implant, and wherein the first plane is generally orthogonal to the second plane.

6. The implant of claim 3, wherein the second anchor hole is an elongated slot.

7. The implant of claim 3, wherein the second anchor hole has a first diameter and further comprising an eccentric bearing having an outer diameter configured to engage the second anchor hole, the eccentric bearing having an inner hole configured to pass the second anchor.

8. The implant of claim 1, wherein the inner shaft is associated with a third anchor hole configured to receive a third anchor therethrough, the third anchor being configured for coupling the adjustable implant to the second portion of bone.

9. The implant of claim 1, wherein the first anchor is a bone screw.

10. The implant of claim 1, wherein the driving element comprises a permanent magnet.

11. The implant of claim 10, wherein the permanent magnet comprises a radially poled rare earth magnet.

12. The implant of claim 1, wherein the driving element is selected from the group consisting of a motor, an inductively coupled motor, an ultrasonically actuated motor, a subcutaneous hydraulic pump, a shape-memory driven actuator, and a piezoelectric element.

13. The implant of claim 1, wherein the non-invasively adjustable implant is configured to change an angle of a tibia of a subject having osteoarthritis of the knee.

14. The implant of claim 13, wherein the non-invasively adjustable implant is configured to adjust a mechanical axis in a lateral direction in relation to a knee joint associated with the tibia.

15. A non-invasively adjustable implant, comprising:
    an outer housing associated with a first anchor hole configured to receive a first anchor therethrough, the first anchor being configured to couple the adjustable implant to a first portion of bone,
    wherein the first anchor hole is slotted with a raised portion located therein, the raised portion being configured to allow the first anchor to pivot in at least a first angular direction,
    wherein the raised portion intersects with, and extends substantially perpendicular to, a central longitudinal axis of the outer housing;
    an inner shaft telescopically disposed in the outer housing, the inner shaft configured to couple to a second portion of bone that is separated from the first portion of bone, such that non-invasive elongation of the adjustable implant causes the inner shaft to extend from the outer housing and to move the first portion of bone relative to the second portion of bone; and
    a driving element disposed within the outer housing and configured to be remotely operable to telescopically displace the inner shaft in relation to the outer housing.

16. The implant of claim 15, wherein the outer housing is associated with a second anchor hole configured to receive a second anchor therethrough, the second anchor being configured to couple the adjustable implant to the first portion of bone.

17. The implant of claim 16, wherein the second anchor hole is configured to allow the second anchor to translate in a first translation direction and a second translation direction opposite the first translation direction.

18. The implant of claim 16, further comprising an eccentric bearing having an outer diameter configured to engage the second anchor hole and an inner hole configured to receive the second anchor.

19. The implant of claim 15, wherein the driving element is selected from the group consisting of a permanent magnet, a motor, an inductively coupled motor, an ultrasonically actuated motor, a subcutaneous hydraulic pump, a shape-memory driven actuator, and a piezoelectric element.

20. The implant of claim 15, wherein raised portion is integrally formed on a surface of the first anchor hole.

* * * * *